US009949870B2

(12) United States Patent
Frankenne et al.

(10) Patent No.: US 9,949,870 B2
(45) Date of Patent: Apr. 24, 2018

(54) INTRA-UTERINE INSERTION DEVICE

(75) Inventors: Francis Frankenne, Chaudfontaine (BE); Vincent Gerkens, Braine L'Alleud (BE)

(73) Assignee: Odyssea Pharma S.P.R.L., Grace-Hollogne (BE)

( * ) Notice: Subject to any disclaimer, the term of this patent is extended or adjusted under 35 U.S.C. 154(b) by 891 days.

(21) Appl. No.: 13/879,706

(22) PCT Filed: Oct. 20, 2011

(86) PCT No.: PCT/EP2011/068364
§ 371 (c)(1),
(2), (4) Date: Apr. 16, 2013

(87) PCT Pub. No.: WO2012/055766
PCT Pub. Date: May 3, 2012

(65) Prior Publication Data
US 2013/0213406 A1 Aug. 22, 2013

Related U.S. Application Data

(60) Provisional application No. 61/408,316, filed on Oct. 29, 2010, provisional application No. 61/453,026, filed on Mar. 15, 2011.

(30) Foreign Application Priority Data

Mar. 15, 2011 (EP) .................................. 11158273

(51) Int. Cl.
*A61F 6/18* (2006.01)
*A61F 6/06* (2006.01)
(Continued)

(52) U.S. Cl.
CPC .................. *A61F 6/18* (2013.01); *A61F 6/06* (2013.01); *A61F 6/14* (2013.01); *A61B 2017/1205* (2013.01); *A61F 6/144* (2013.01)

(58) Field of Classification Search
CPC ...... A61F 6/00; A61F 6/06; A61F 6/14; A61F 6/142; A61F 6/144; A61F 6/146;
(Continued)

(56) References Cited

U.S. PATENT DOCUMENTS 494,973 A 4/1893 Armstrong
3,965,891 A * 6/1976 Lerner ...................... A61F 6/18
128/840
(Continued)

FOREIGN PATENT DOCUMENTS

DE 19815552 C1 9/1999
JP 53-120882 10/1978
(Continued)

OTHER PUBLICATIONS

International Search Report for International Application No. PCT/EP2011/068364, dated Jul. 25, 2012.
(Continued)

*Primary Examiner* — Keri J Nelson
(74) *Attorney, Agent, or Firm* — Knobbe, Martens, Olson & Bear, LLP

(57) ABSTRACT

The present invention relates to an inserter (100), having a proximal (20) and distal (30) end, for inserting and positioning an intra-uterine device (IUD) (120), which is attached to a withdrawal string (130), said inserter (100) comprising: a) a plunger (102), having a central longitudinal axis, configured for slidable mounting of a hollow protective tube (110), the distal (30) end of the plunger (102) being configured for dismountable connection with the IUD (120), which protective tube (110) is configured to slidably cover the IUD (120); b) a handle (104), which is attached to the proximal (20) end of the plunger (102); and c) a longitudinal member (150) that forms part of the handle (104), which extends in the distal (30) direction with respect to the
(Continued)

plunger (102), which longitudinal member (150) contains a friction contact surface (152) against which the protective tube (110) can frictionally engage, wherein the frictional engagement of the friction contact surface (152) against the protective tube (110) is manually actuatable and wherein the frictional engagement of the friction contact surface (152) against the protective tube (110) increases resistance to sliding of the protective tube (110) relative to the plunger (102).

14 Claims, 24 Drawing Sheets

(51) Int. Cl.
*A61B 17/12* (2006.01)
*A61F 6/14* (2006.01)

(58) Field of Classification Search
CPC ...... A61F 6/18; A61F 6/20; A61F 6/22; A61F 6/225; A61B 17/00; A61B 17/12022; A61B 17/1205; A61B 2017/1205
USPC ........... 128/830–833, 839–840; 604/48, 500, 604/506, 514, 515
See application file for complete search history.

(56) References Cited

U.S. PATENT DOCUMENTS

| | | | | |
|---|---|---|---|---|
| 4,143,656 | A * | 3/1979 | Holmes | 128/840 |
| 4,721,105 | A * | 1/1988 | Wildemeersch | 128/840 |
| 4,949,732 | A * | 8/1990 | Spoon et al. | 128/839 |
| 6,588,429 | B1 * | 7/2003 | Wildemeersch | 128/830 |
| 8,573,222 | B2 * | 11/2013 | Weintraub | A61F 6/144 |
| | | | | 128/833 |
| 2011/0162656 | A1 | 7/2011 | Jutila et al. | |
| 2011/0166508 | A1 | 7/2011 | Lyytikainen et al. | |
| 2011/0172593 | A1 | 7/2011 | Lyyikainen et al. | |

FOREIGN PATENT DOCUMENTS

| | | |
|---|---|---|
| JP | 10-510444 | 10/1998 |
| WO | WO 96/18365 | 6/1996 |

OTHER PUBLICATIONS

Japanese Office Action; Application No. JP 2013-535374; dated Aug. 18, 2015.

* cited by examiner

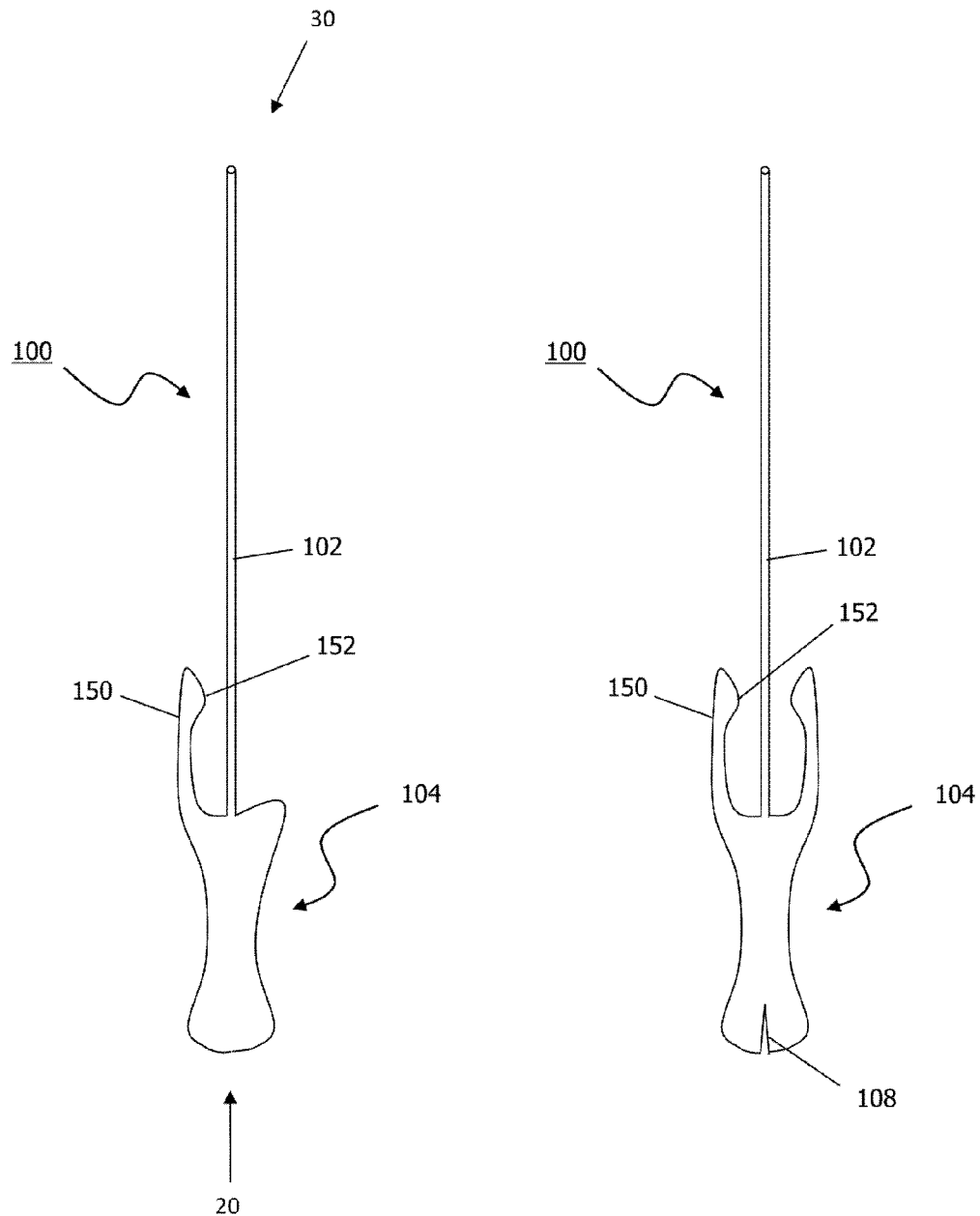

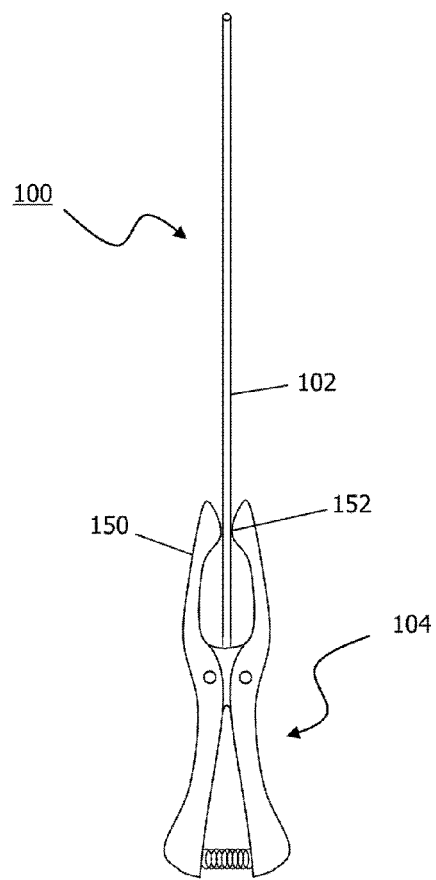
FIG. 3
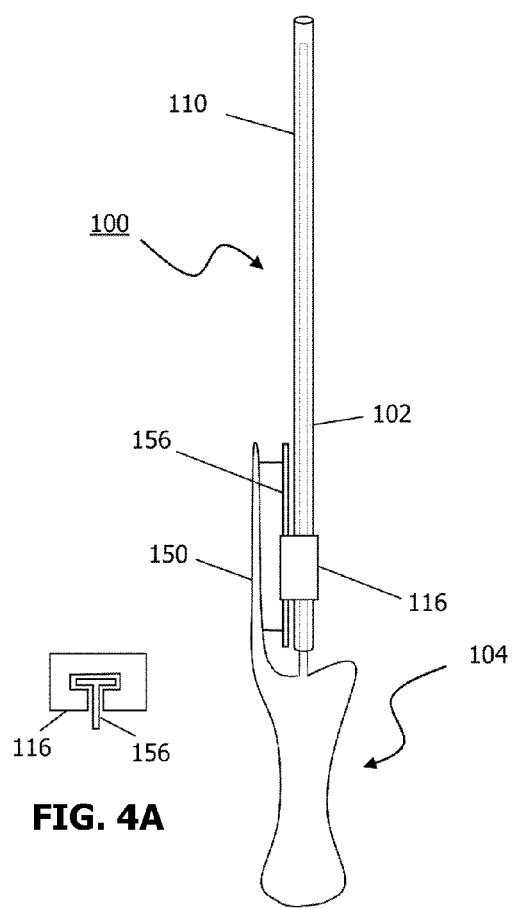
FIG. 4A
FIG. 4

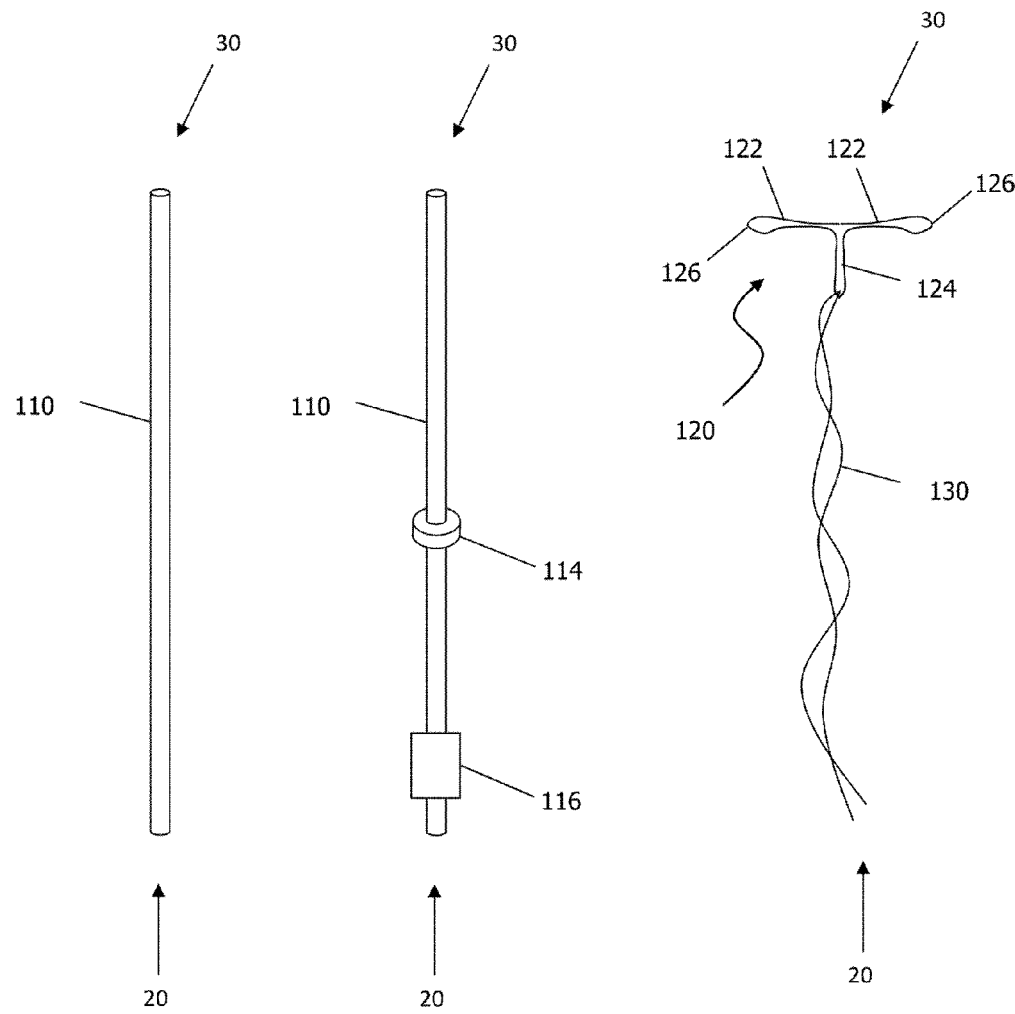

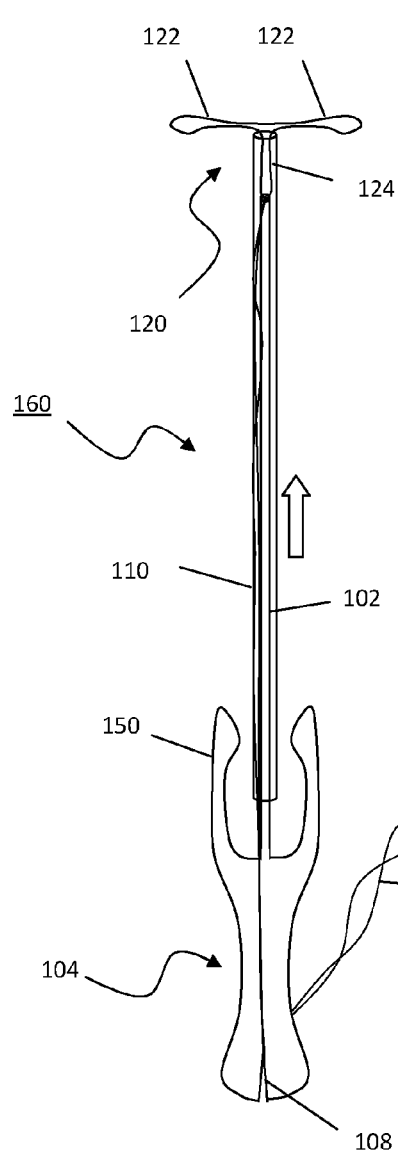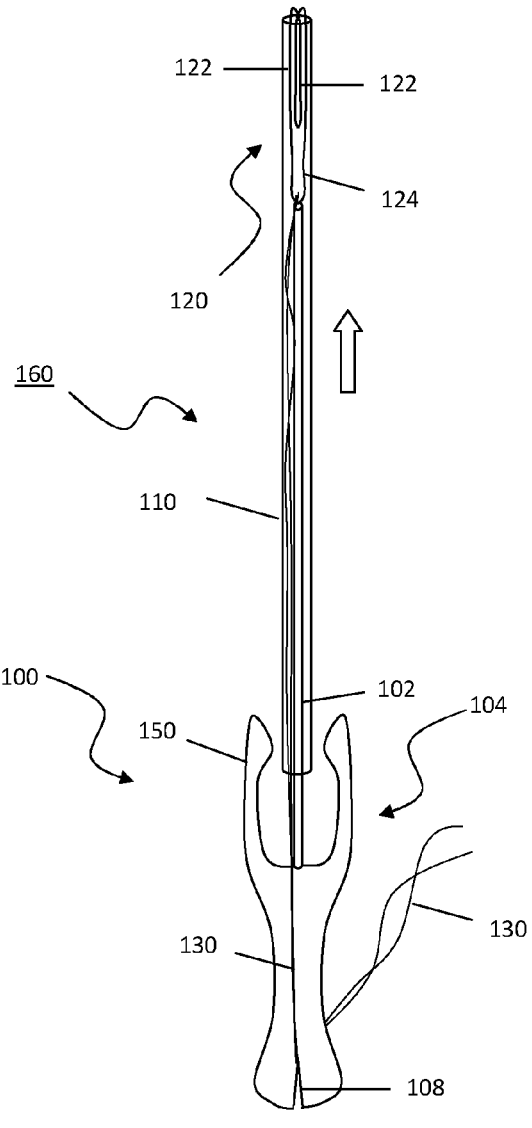
FIG. 14  FIG. 15

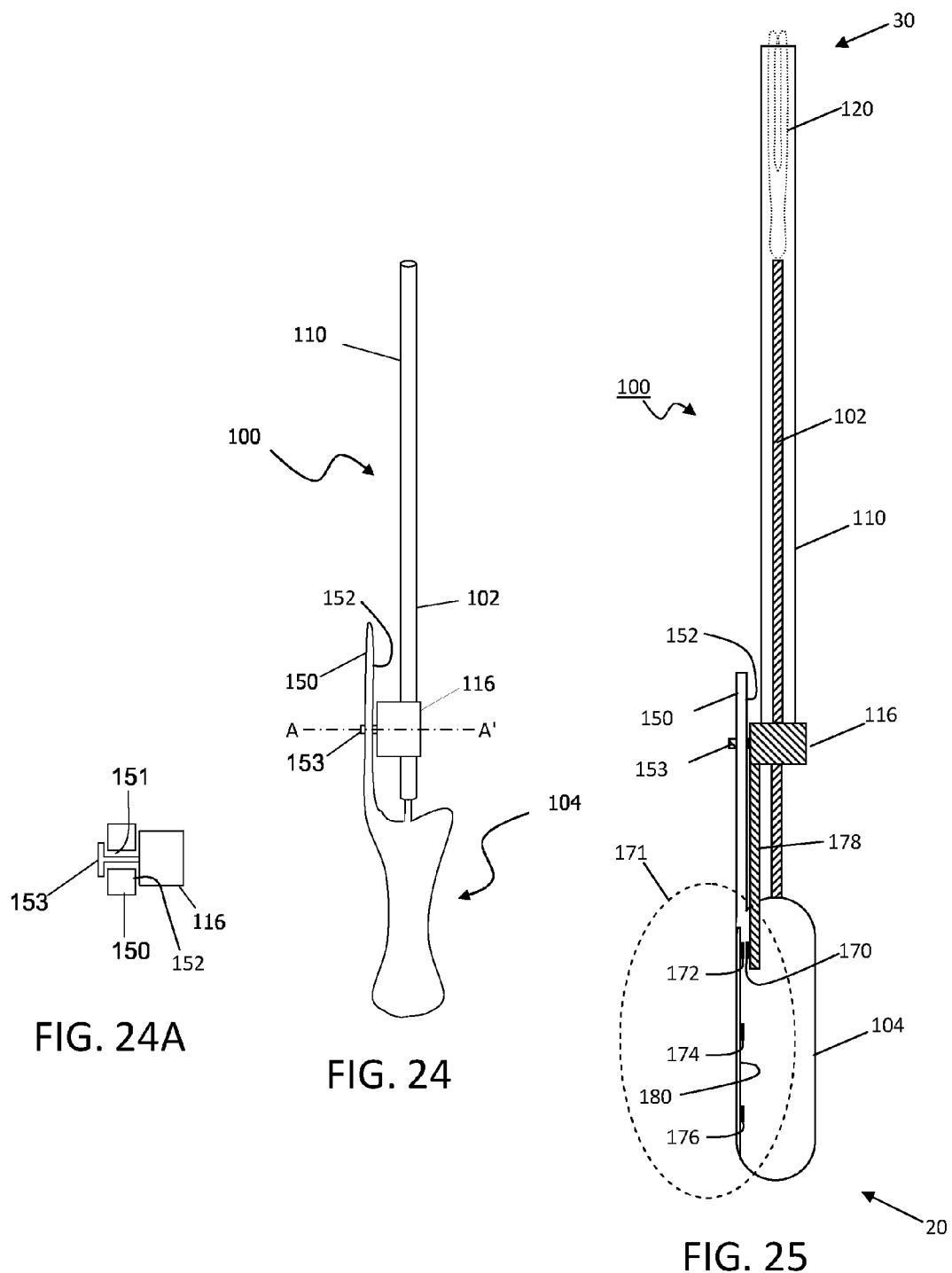

INTRA-UTERINE INSERTION DEVICE

CROSS-REFERENCE TO RELATED APPLICATIONS

This application is the U.S. National Phase under 35 U.S.C. § 371 of International Application PCT/EP2011/068364, filed Oct. 20, 2011, which claims priority to U.S. Provisional Application 61/408,316, filed Oct. 29, 2010, EP 11158273.0, filed Mar. 15, 2011 and U.S. Provisional Application 61/453,026 filed Mar. 15, 2011.

FIELD OF THE INVENTION

The invention relates to apparatuses and methods for inserting intra-uterine devices (IUDs).

BACKGROUND OF THE INVENTION

Hormonal or copper intra-uterine devices (IUDs) or intra-uterine systems (IUSs) are used as a common method of anti-conception and/or for treatment of menorrhagia and/or for treatment of other conditions. The term IUD (intra-uterine device) will be used herein to refer to both IUDs and IUSs.

IUDs are commonly T-shaped, having an elongated member (from hereon called the central rod) having at one end a transverse member comprising two wings. The wing tips (also known as hands) at the end of these wings may be rounded off. The central rod and the wings form a substantially T-shaped piece when the device is positioned in the uterus. In addition to a T-shape, IUDs also exist in other shapes such as a ring, a rod, a '7' or an 'S'.

The intra-uterine device (IUD) can be partially or wholly made from plastic material, biocompatible material or metal, such as silver or gold, and sometimes contains a copper wire wound partly around it. The copper ions that are released act as a spermicide, further enhancing the contraceptive properties of the IUD. Intra-uterine devices are also capable of releasing drugs, hormones (such as levonorgestrel) or other active agents to treat menorrhagia or other conditions.

Intra-uterine devices often have a withdrawal string attached to the central rod of the device. After insertion of an IUD, the string remains positioned within the cervix for a period of up to 5 to 10 years to facilitate extraction of the IUD by the health care provider. The withdrawal string also allows the patient to check whether the IUD is still correctly in place.

The IUD and string are introduced into the uterus by means of a separate inserter device. Several types of inserter devices exist in the prior art. Most common inserters are constructed for introducing the IUD in a contracted and covered state during insertion in order to facilitate the introduction of the IUD into the cervical canal. Typically, this covered state is provided by a protective tube, in which the IUD can be housed during insertion. In addition, the protective tube usually has a rounded, blunt end which will pass through the cervical canal easily and which will not damage the fundus of the uterus upon contact therewith.

However, because of the delicate nature of the insertion procedure, existing inserters are often inefficient in handling, which is mainly due to the various moving parts. Production costs are relatively high because of the different parts that need to be assembled correctly. Furthermore, the more complicated the device assembly, the higher the demands and costs are for quality control.

Several IUD inserters contain a stopping mechanism, facilitating correct positioning of the IUD within the uterus. However, these stops are discrete and only tailored to the insertion of one particular IUD with a specific size and shape. Therefore, the same inserter cannot be used to insert an IUD that differs in shape or size. Discrete stops also prevent fine-tuning by the medical practitioner, who is confined to a limited set of specific configurations.

Therefore, the main objective of the current invention is to provide an inserter device suitable for inserting a conventional intra-uterine device (IUD) connected to a withdrawal string, said inserter device being inexpensive to produce and easy to use, yet still ensuring accurate and safe insertion of the IUD. Furthermore, said inserter device should be practical for insertion of a range of IUDs, without any structural modifications to the inserter necessary.

It is an objective of the current invention to provide an inserter that is inexpensive and easy to produce on a large scale. Another objective of the current invention is to provide an inserter that comprises a minimum of moving parts and separate parts. Another objective of the current invention is to provide an inserter that is low cost and can therefore provide contraception to a global market, third-world countries in particular. Another objective of the current invention is to provide an inserter unlikely to break, safe to use and unlikely to harm the patient. Another objective of the current invention is to provide an inserter that is easy to use, therefore allowing for lesser trained professionals to insert the device. Another objective of the current invention is to provide an inserter that allows correct positioning of the IUD within the uterus. Another objective of the current invention is to provide an inserter that provides an infinite number of insertion positions, whereby the correct insertion position can be tailored to the IUD to be inserted. Another objective of the current invention is to provide an inserter that allows easy manipulation and fixation of the withdrawal string during the insertion procedure. Another objective of the current invention is to provide an inserter that is designed primarily for the insertion of conventional devices which are to be inserted in a compressed configuration. The invention as described in this application, and preferred embodiments thereof, will comply with one or more of the above-mentioned objectives.

SUMMARY OF THE INVENTION

The present invention relates to an inserter (100) having a proximal (20) and distal (30) end, for inserting and positioning an intra-uterine device (IUD) (120), which is attached to a withdrawal string (130), said inserter (100) comprising:

a) a plunger (102), having a central longitudinal axis, configured for slidable mounting of a hollow protective tube (110), the distal (30) end of the plunger (102) being configured for dismountable connection with the IUD (120), which protective tube (110) is configured to slidably cover the IUD (120);

b) a handle (104), which is attached to the proximal (20) end of the plunger (102); and c) a longitudinal member (150) that forms part of the handle (104), which extends in the distal (30) direction with respect to the plunger (102), which longitudinal member (150) contains a friction contact surface (152) against which the protective tube (110) can frictionally engage, whereby the frictional engagement of the friction contact surface (152) against the protective tube (110) is manually actuateable and whereby the frictional engagement of the friction contact surface (152) against the protective tube (110) regulates resistance to sliding of the protective tube (110) relative to the plunger (102).

The longitudinal member (150) is preferably compliant or hinged, the longitudinal member (150) being configured to apply a force to the protective tube (110) upon manual actuation of the longitudinal member (150), which force is in an essentially radial direction relative to the central longitudinal axis of the plunger (102).

The handle (104) may be disposed with two longitudinal members (150), the two longitudinal members (150) being diametrically arranged around the central longitudinal axis of the plunger (110), and the two longitudinal members (150) being configured to apply essentially diametrically opposing radial forces to the protective tube (110) upon manual actuation of the two longitudinal members (150).

The longitudinal member (150) may be pivoted with respect to the plunger (102), being configured to apply a force to the protective tube (110), which force is in an essentially radial direction relative to the central longitudinal axis of the plunger (102), and said radial force is reduced upon manual actuation of the longitudinal member (150).

The handle (104) may be disposed with two longitudinal members (150), the two longitudinal members (150) being diametrically arranged around the central longitudinal axis of the plunger (102), and the two longitudinal members (150) being configured to apply essentially diametrically opposing radial forces to the protective tube (110), which radial forces are reduced upon manual actuation of the two longitudinal members (150).

The longitudinal member (150) is preferably in essentially fixed relation to the plunger (102), being configured to receive a force in an essentially radial direction relative to the central longitudinal axis of the plunger (102), wherein the force is applied by the protective tube (110) upon manual actuation of the protective tube (110).

The friction contact surface (152) may comprise a longitudinal guiding rail (156), wherein the protective tube (110) is provided at the proximal (20) end with a cuff (116), and wherein the longitudinal guiding rail (156) and the cuff (116) are slidably connected. The longitudinal guiding rail (156) preferably has a T-shaped profile and the cuff (116), a reciprocating T-shaped slot, through which slot the longitudinal guiding rail (156) slides, allowing the protective tube (110) to slide relative to the longitudinal member (150).

The friction contact surface (152) may comprise a longitudinal guiding rail (156), wherein the protective tube (110) is provided at the proximal (20) end with a cuff (116), and wherein the longitudinal guiding rail (156) and the cuff (116) are slidably connected. The longitudinal member (150) may comprise a longitudinal guiding slot (151) and the cuff (116) disposed with a T-shaped protrusion (153), slot along which the T-shaped protrusion (153) slidably engages, allowing the protective tube (110) to slide relative to the longitudinal member (150). The friction contact surface (152) and/or the surface of the plunger (102) may comprise serrations (154), configured to improve resistance to sliding of the protective tube (110) relative to the plunger (102) upon frictional engagement.

The plunger (102) and handle (104) may form one piece, wherein the plunger (102) is at least partially solid, and wherein the handle (104) may comprise a fastening means (108) configured to secure the withdrawal string (130), optionally under tension. The plunger (102) may be disposed with a longitudinal groove for receiving the withdrawal string (130). The plunger may terminate in a distal tip configured to dismountably couple to the proximal (20) end of the central rod (124) of the IUD (120).

The inserter may further comprise the protective tube (110) having a central lumen, through which the plunger (102) is disposed, wherein the distal (30) end of the protective tube (110) is configured for receiving the intra-uterine device (IUD) (120).

The protective tube (110) may further comprises a flange (114), optionally slidable, on the surface of the protective tube (110), configured to abut with the entrance of the cervix (210) to prohibit further insertion of the protective tube (110) into the uterine cavity (222).

The IUD (120) may be a T-shaped IUD comprising a pair of wings (122) each having a rounded wing tip, which wings fixed to a central rod (124), said IUD (120) positioned at the distal (30) end of the plunger (102); and the protective tube (110) may be attached in fixed relation to a first discrete contact element (170) and the plunger (102) may be attached in fixed relation to a second discrete contact element (172), the first (170) and second (172) discrete contact elements being in slidable relation to each other and configured such that they frictionally engage together so increasing the resistance to sliding of the protective tube (110) relative to the plunger (102) selectively at a first discrete position (P1) which corresponds to a position of the protective tube (110) where it covers at least part of the wings (122) of the IUD (120) when the central rod (124) of the IUD (120) is engaged with the distal (30) end of the plunger (102). The IUD (120) may be a T-shaped IUD comprising a pair of wings (122) each having a rounded wing tip, which wings are fixed to a central rod (124), said IUD (120) positioned at the distal (30) end of the plunger (102); and the protective tube (110) may be attached in fixed relation to a third discrete contact element (170') and the plunger attached in fixed relation to a fourth discrete contact element (174), the third (170') and fourth (174) discrete contact elements being in slidable relation to each other and configured such that they engage together so increasing the resistance to sliding of the protective tube (110) relative to the plunger (102) selectively at a second discrete position (P2) which corresponds to a location of the protective tube (110) where it covers at least part of the IUD (120) central rod, and the wings are unfolded when the central rod (124) of the IUD (120) is engaged with the distal (30) end of the plunger (102).

The first (170) and third (170') discrete contact elements may be one and the same.

The IUD (120) may be a T-shaped IUD comprising a pair of wings (122) each having a rounded wing tip, which wings are fixed to a central rod (124), said IUD (120) positioned at the distal (30) end of the plunger (102); and The protective tube (110) may be attached in fixed relation to a fifth discrete contact element (170") and the plunger (102) attached in fixed relation a sixth discrete contact element (176), the fifth discrete contact element (170") and sixth discrete contact element (176) being in slidable relation to each other and configured such that they engage, so stopping the sliding of the protective tube (110) relative to the plunger (102) selectively at a third discrete position (P3) which corresponds to a location of protective tube where IUD (120) central rod is uncovered when the central rod (124) of the IUD (120) is engaged with the distal (30) end of the plunger (102).

The first (170), third (170') and fifth (170") discrete contact elements may be one and the same.

The invention also provides inserter (100) assembly, comprising:
- an inserter according to as described herein,
- a protective tube (110) having a central lumen, through which the plunger (102) is disposed, wherein the distal (30) end of the protective tube (110) is configured for receiving the intra-uterine device (IUD) (120),
- a T-shaped intra-uterine device (IUD) (120) comprising a pair of wings (122) each having a rounded wing tip, which wings fixed to a central rod (124), said IUD (120) positioned at the distal (30) end of the plunger (102), wherein the IUD further comprises a withdrawal string (130) attached at one end, preferably to the rod (124), wherein the withdrawal string (130) passes through the central lumen of the protective tube (110) from the distal (30) end to the proximal (20) end.

The wings (122) of the IUD (120) are preferably configured to fold or unfold responsive to the slidable movement of the protective tube (110) that can cover or uncover the wings (122) of the IUD (120).

The protective tube (110) preferably further comprises a flange (114), optionally slidable, on the surface of the protective tube (110), configured to abut with the entrance of the cervix (210) to prohibit further insertion of the protective tube (110) into the uterine cavity (222).

The present invention further relates to an inserter (100) suitable for inserting and positioning an intra-uterine device (IUD) (120), which is attached to a withdrawal string (130), comprising:
- a) a plunger (102), having a proximal (20) and distal (30) end, over which the protective tube (110) can slide, which distal (30) end is configured for dismountable connection with the IUD (120), which protective tube (110) is configured to slidably cover the IUD (120);
- b) a handle (104), which is attached to the proximal end of the plunger (102) and which further comprises a tong-shaped gripping mechanism (106); and whereby the gripping mechanism (106) is adapted to reversibly lock the position of the protective tube (110) relative to the plunger (102).

The inserter (100) preferably further comprises the protective tube (110) having a central lumen, through which the plunger (102) is disposed, whereby the distal (30) end of the protective tube (110) is shaped for facilitating insertion of the intra-uterine device (IUD) (120). The inserter (100) preferably further comprises a T-shaped intra-uterine device (IUD) (120) comprising a pair of wings (122) fixed to a central rod (124), positioned at the distal (30) end of the plunger (102).

The invention also relates to a further method for priming for insertion into the cervical canal (222) an inserter assembly provided with an IUD (120) positioned with the wings (110) outside the protective tube (110) comprising the steps:
- a) keeping the withdrawal string (130) relaxed;
- b) advancing partially the protective tube (110) distally over the plunger (102) until the protective tube (110) is positioned such that the wing tips of the IUD (120) would partially protrude from the protective tube (110) but are touching when the central rod of the IUD (120) is engaged with the distal (30) end of the plunger (102);
- c) activating frictional engagement of the friction contact surface (152) against the protective tube (110), so as to fix the position of the protective tube (110) relative to the plunger (102); and
- d) providing tension to the withdrawal string (130), wherein the IUD (120) enters inside the central lumen of the protective tube until the wings (122) of the IUD are covered by the protective tube (110) and the wing tips (126) of the IUD (120) partially protrude (preferably are half out) from the protective tube (110) but are touching, and the proximal (20) end of the IUD (120) is engaged with the distal (30) end of the plunger (102);
- e) thereby priming the inserter assembly.

The invention also relates to a method for priming for insertion into the cervical canal (222) an inserter assembly provided with an IUD (120) positioned with the wings (110) outside the protective tube (110) comprising the steps:
- a) keeping the withdrawal string (130) relaxed;
- b) advancing partially the protective tube (110) distally over the plunger (102) until the protective tube (110) is positioned such that the wing tips of the IUD (120) would partially protrude from the protective tube (110) but are touching when the central rod of the IUD (120) is engaged with the distal (30) end of the plunger (102);
- c) activating frictional engagement of the friction contact surface (152) against the protective tube (110), so as to fix the position of the protective tube (110) relative to the plunger (102); and
- d) providing tension to the withdrawal string (130), wherein the IUD (120) enters inside the central lumen of the protective tube until the wings (122) of the IUD are covered by the protective tube (110) and the wing tips (126) of the IUD (120) partially protrude (preferably are half out) from the protective tube (110) but are touching, and the proximal (20) end of the IUD (120) is engaged with the distal (30) end of the plunger (102);
- e) thereby priming the inserter assembly.

The invention also relates to a further method for inserting and positioning an intra-uterine device (IUD) (120) by use of an inserter (100) as defined herein, said method comprising the following steps:
- a) covering the IUD (120) with a protective tube (110), while keeping the withdrawal string (130) relaxed;
- b) partially advancing the inserter (100) into the cervical canal, while activating the gripping mechanism (106), while keeping the withdrawal string under tension;
- c) partially withdrawing the protective tube (110), while de-activating the gripping mechanism (106), while keeping the withdrawal string (130) under tension, such that the wings (122) of the IUD (120) are uncovered from the protective tube (110);
- d) fully advancing the inserter (100) into the cervical canal, while activating the gripping mechanism (106), while keeping the withdrawal string (130) under tension; and
- e) fully withdrawing the inserter (100), while activating the gripping mechanism (106), while releasing the tension on the withdrawal string (130).

The invention also relates to the use of an inserter (100) as described by the aforementioned embodiments for insertion of an IUD.

BRIEF DESCRIPTION OF THE DRAWINGS

FIG. 1: provides a schematic representation of the main elements of the inserter device (100).

FIG. 2: provides a schematic representation of optional elements of the inserter device (100) according to an embodiment of the invention, whereby two longitudinal members (150) are diametrically arranged around the central longitudinal axis of the plunger (110), and whereby the two longitudinal members (150) are configured to apply diametrically opposing radial forces to the protective tube (110) upon manual actuation of the two longitudinal members (150).

FIG. 3: provides a schematic representation of optional elements of the inserter device (100) according to an embodiment of the invention, whereby two longitudinal members (150) are diametrically arranged around the central longitudinal axis of the plunger (110), and whereby the two longitudinal members (150) are configured to apply diametrically opposing radial forces to the protective tube (110), which radial forces are reduced upon manual actuation of the two longitudinal members (150).

FIG. 4: provides a schematic representation of optional elements of the inserter device (100) according to an embodiment of the invention, whereby the friction contact surface (152) comprises a longitudinal guiding rail (156), whereby the protective tube is provided at the proximal (20) end with an overmolding (116), and whereby the longitudinal guiding rail (156) and the overmolding (116) are slidably connected.

FIG. 4A: shows a cross-sectional view of the overmolding (116) and guiding rail (156) in a plane perpendicular to the longitudinal axis of the plunger (110).

FIG. 5: provides a schematic representation of optional elements of the inserter device (100) that is a protective tube (110).

FIG. 6: provides a schematic representation of optional elements of the inserter device (100) that is a protective tube (110) provided with a flange and cuff.

FIG. 7: provides a schematic representation of optional elements of the inserter device (100) that is an intra-uterine device (120), optionally attached to a withdrawal string (130).

FIGS. 12 to 15 show a schematic illustration of steps of an alternative method for priming an IUD (120) attached to a withdrawal string (130) using a preferred embodiment of the inserter device (100) and a protective tube (110).

FIGS. 24 and 24A show a particular inserter of the invention provided with a single longitudinal member provided with a guiding slot, and a cuff of the protective tube which slidably engages the slot. FIG. 24A depicts a transverse cross-section through a plane along line A-A'.

FIG. 25 depicts a view of an inserter provided with a guiding slot, and a cuff of the protective tube which slidably mounts the slot, and with a plurality of discrete contact elements disposed in the handle. An enlarged view of the encircled area 171 is given in FIGS. 26, 26A, 27, 27A, and 28, 28A with alternative configurations.

DETAILED DESCRIPTION OF THE INVENTION

Figure 8:
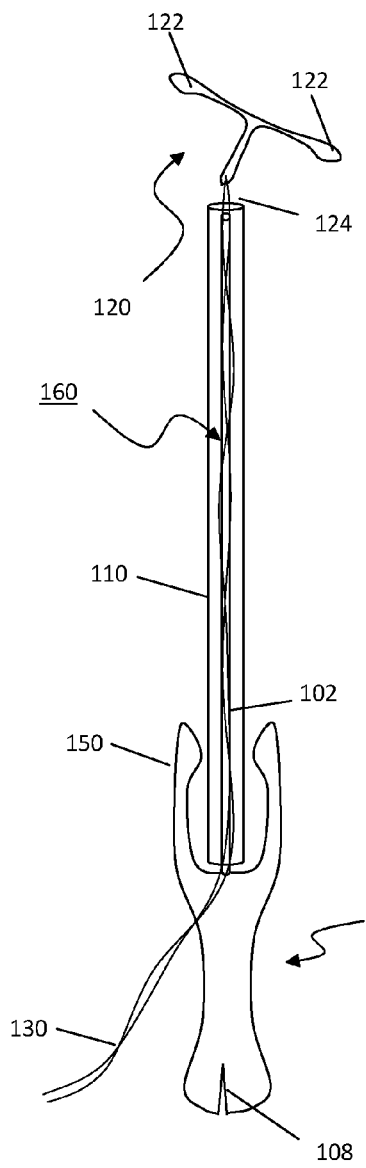
FIGS. 8 to 11 show a schematic illustration of steps of a method for priming an IUD (120) attached to a withdrawal string (130) using a preferred embodiment of the inserter device (100) and a protective tube (110).
Figure 9:
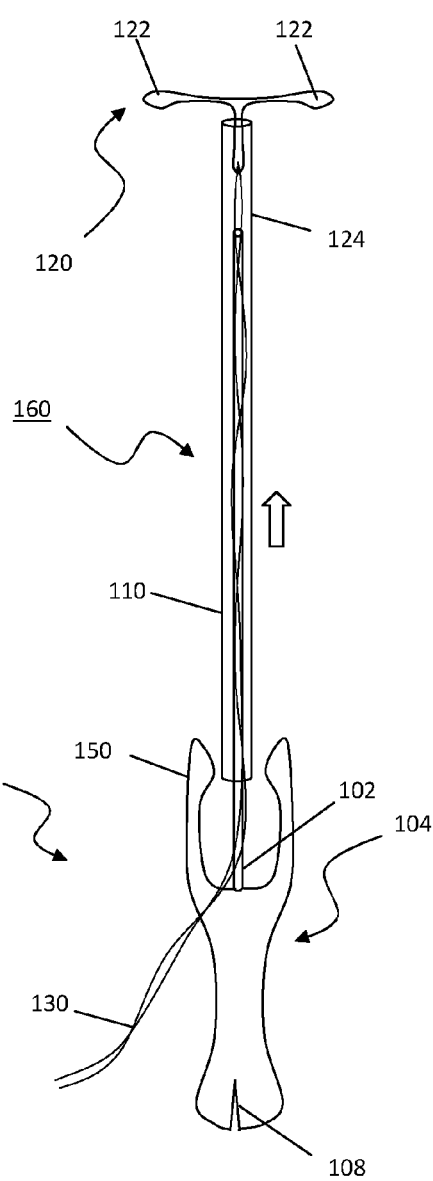
Figures 10, 11:
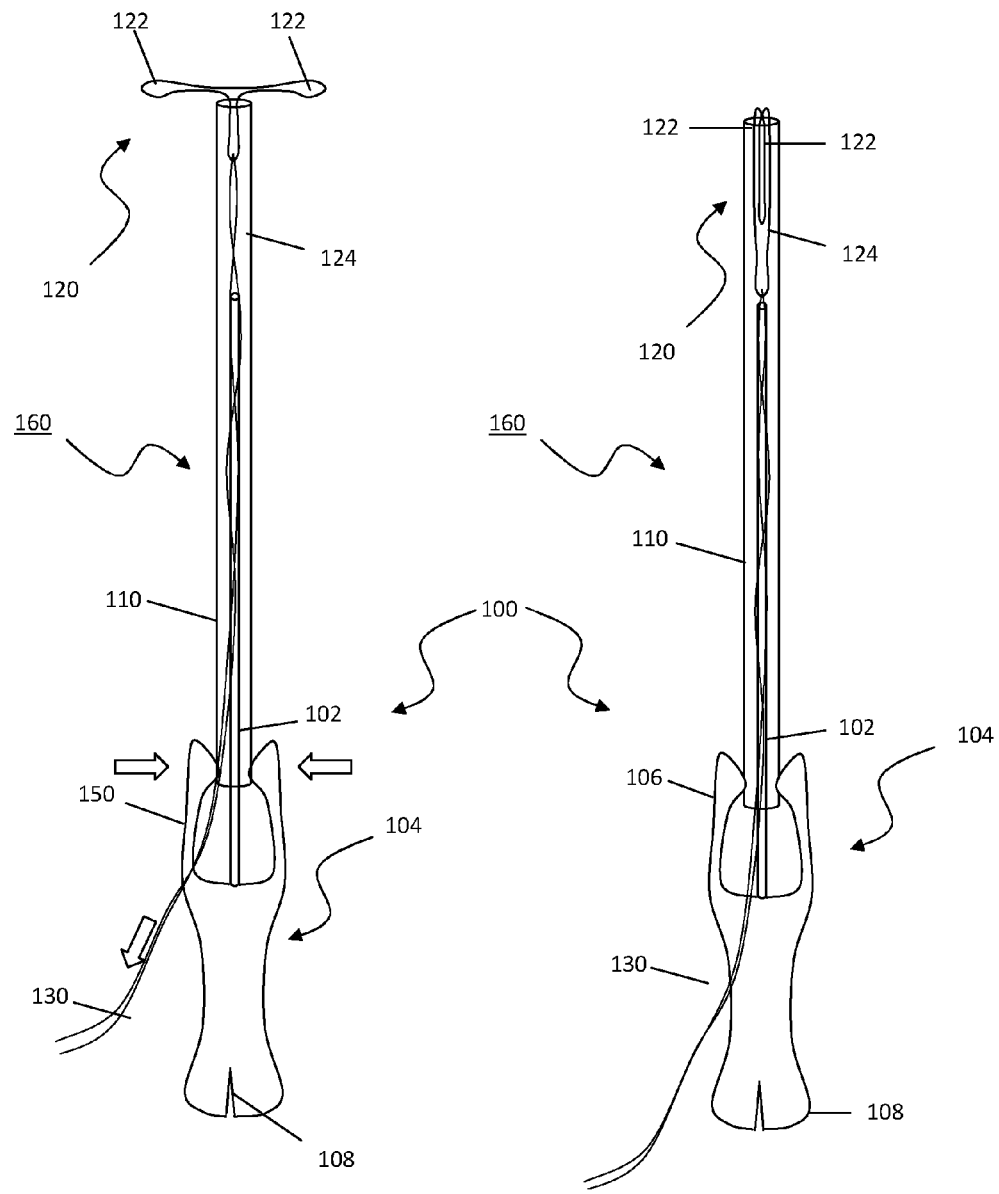

Unless defined otherwise, all technical and scientific terms used herein have the same meaning as is commonly understood by one of skill in the art. All publications referenced herein are incorporated by reference thereto.

The articles 'a' and 'an' are used herein to refer to one or to more than one, i.e. to at least one of the grammatical object of the article.

Throughout this application, the term 'about' is used to indicate that a value includes the standard deviation of error for the device or method being employed to determine the value.

The recitation of numerical ranges by endpoints includes all integer numbers and, where appropriate, fractions subsumed within that range (e.g. 1 to 5 can include 1, 2, 3, 4 when referring to, for example, a number of elements). The recitation of end points also includes the end point values themselves (e.g. from 1.0 to 5.0 includes both 1.0 and 5.0).

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

The terms "distal", "distal end", "proximal" and "proximal end" are used through the specification, and are terms generally understood in the field to mean towards (proximal) or away (distal) from the practitioner side of the apparatus. Thus, "proximal (end)" means towards the practitioner side and, therefore, away from the patient side. Conversely, "distal (end)" means towards the patient side and, therefore, away from the practitioner side.

In the following detailed description of the invention, reference is made to the accompanying drawings that form a part hereof, and in which are shown by way of illustration only of specific embodiments in which the invention may be practiced. It is to be understood that other embodiments may be utilized and structural or logical changes may be made without departing from the scope of the present invention.

With reference to FIG. 1 the present invention provides an inserter (100), having a proximal (20) and distal (30) end, for inserting and positioning an intra-uterine device (IUD) (120), which is attached to a withdrawal string (130), said inserter (100) comprising:
  a) a plunger (102), having a central longitudinal axis, configured for slidable mounting of a hollow protective tube (110), the distal (30) end of the plunger (102) being configured for dismountable connection with the IUD (120), which protective tube (110) is configured to slidably cover the IUD (120);
  b) a handle (104), which is attached to the proximal (20) end of the plunger (102); and
  c) a longitudinal member (150) that forms part of the handle (104), which extends in the distal (30) direction with respect to the plunger (102), which longitudinal member (150) is shorter than the plunger (102), which longitudinal member (150) contains a friction contact surface (152) against which the protective tube (110) can frictionally engage,
wherein the frictional engagement of the friction contact surface (152) against the protective tube (110) is manually actuatable and wherein the frictional engagement of the friction contact surface (152) against the protective tube (110) regulates (increases) resistance to sliding of the protective tube (110) relative to the plunger (102).

Manual actuation of the longitudinal member (150) may occur via manual actuation of the handle (104), of which the longitudinal member (150) forms part.

The longitudinal member (150) may be compliant or hinged with respect to the handle (104). It may be actuated to move radially, relative to the longitudinal axis of the plunger (102). In particular, the distal end of the longitudinal member may be actuated to move radially, relative to the longitudinal axis of the plunger (102), by the application of force to the distal end of the longitudinal member. Thus, the longitudinal member (150) is configured to apply a force to the protective tube (110) upon manual actuation of the longitudinal member (150), which force is in a radial direction relative to the central longitudinal axis of the plunger (102). Examples of such configuration is given in FIG. 2.

The handle (104) may be disposed with two longitudinal members (150), whereby the two longitudinal members (150) are diametrically arranged around the central longitudinal axis of the plunger (110), and whereby the two longitudinal members (150) are configured to apply diametrically opposing radial forces to the protective tube (110) upon manual actuation of the two longitudinal members (150). An example of an inserter according to this embodiment is illustrated in FIG. 2.

Where there are two longitudinal members (150), they may be comprised in a tong-shaped gripping mechanism. Thus, in an embodiment, the invention provides an inserter (100) suitable for inserting and positioning an intra-uterine device (IUD) (120) which is attached to a withdrawal string (130) comprising:
  a) a plunger (102), having a proximal (20) and distal (30) end, over which the protective tube (110) can slide, which distal (30) end is configured for dismountable connection with the IUD (120), which protective tube (110) is configured to slidably cover the IUD (120);
  b) a handle (104), which is attached to the proximal (20) end of the plunger (102) and which further comprises a tong-shaped gripping mechanism.
whereby the gripping mechanism is adapted to reversibly lock the position of the protective tube (110) relative to the plunger (102). The gripping mechanism is preferably shaped like a set of tongs (or like a pair of claws or tweezers). The gripping mechanism is preferably configured such that the radial force is applied when the tongs are squeezed, and the radial force is released when the tongs are released. In a preferred embodiment, the inserter (100) is characterized in that the gripping mechanism (106) is configured to apply a hand-activated force in a radial direction relative to a central longitudinal axis of the protective tube (110) that reversibly locks the slidable position of the protective tube (110) relative to the plunger (102). In a preferred embodiment, the gripping mechanism (102) applies diametrically opposing radial forces to the protective tube (110). The tongs incorporate a spring (i.e. the arms of the tong may be complaint) which maintains the arms of the tongs in an open (released) position. An example of an inserter (100) according to this embodiment is illustrated in FIG. 2.

According to one embodiment of the invention, the longitudinal member (150) is pivoted with respect to the handle (104). It may be actuated to move radially, relative to the longitudinal axis of the plunger (102). In particular, the distal end of the longitudinal member may be actuated to move radially, relative to the longitudinal axis of the plunger (102), by the application of force to the proximal end of the longitudinal member. An example of an inserter (100) according to this embodiment is illustrated in FIG. 3.

As exemplified in FIG. 3, the longitudinal member (150) may be configured to apply a force to the protective tube (110), which force is in a radial direction relative to the central longitudinal axis of the plunger (102), and said radial force is reduced upon manual actuation of the longitudinal member (150). The longitudinal member is a lever i.e. is pivoted. The distal end of the longitudinal member is provided with the friction contact surface (152), while the proximal end is a manual actuation end. Radial force applied to the proximal end (manual actuation end) in a direction towards the central longitudinal axis of the plunger (102) moves the friction contact surface (152) at the distal end in a radial direction away from the central longitudinal axis of the plunger (102). The fulcrum is disposed between the distal and proximal ends of the longitudinal member. Thus squeezing the lever at one end, leads to frictional release at the other end. The pivoted, longitudinal member may incorporate a spring which maintains the friction contact surface (152) a closed (clamping) position. In a preferred embodiment of the invention, the handle (104) is disposed with two such pivoted longitudinal members (150), whereby the two longitudinal members (150) are diametrically arranged around the central longitudinal axis of the plunger (110), and whereby the two longitudinal members (150) are configured to apply diametrically opposing radial forces to the protective tube (110), which radial forces are reduced upon manual actuation of the two longitudinal members (150). Such arrangement may bear a resemblance to a pair of sprung-closed pliers.

Figure 23:
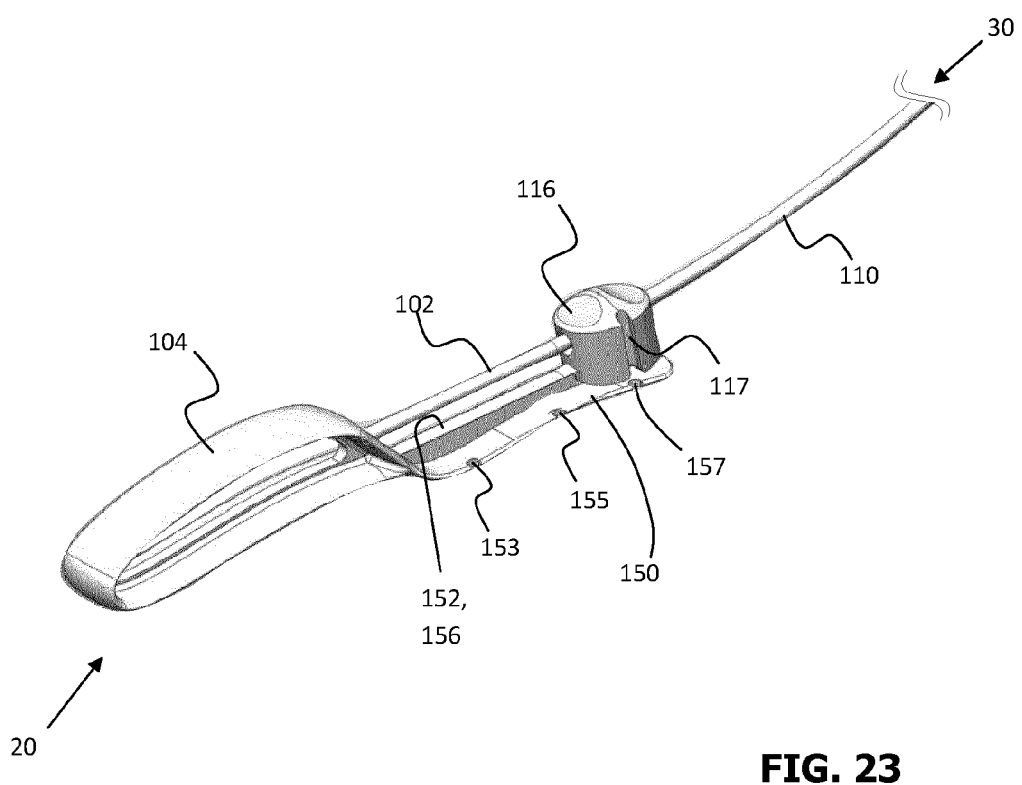
FIG. 23 shows a particular inserter of the invention provided with a single longitudinal member and a guiding rail onto which a cuff of the protective tube slidably mounts. The distal end of the plunger and protective tube is truncated.

According to another embodiment of the invention, the longitudinal member (150) is in essentially fixed relation to the plunger (102). It may be rigid, and rigidly attached at the proximal (20) end to the handle (104). The longitudinal member (150) is configured to receive a force in a radial direction relative to the central longitudinal axis of the plunger (102), whereby the force is applied by the protective tube (110) upon manual actuation of the protective tube (110). An example of an inserter according to this embodiment is illustrated in FIGS. 4, 24 and 24A. Thus, application of a radial force on the protective tube (110) at one diametric point is transmitted through to the other diametric point of the protective tube (110), to the longitudinal member (150) which receives the force. This radial force may be achieved, for instance, by gripping the protective tube (110) using the thumb and the longitudinal member (150) by a finger. The protective tube (110) may be provided with a cuff (116) or overmolding that receives the force of the thumb. The frictional engagement of the friction contact surface (152) of the longitudinal member (150) against the protective tube (110) regulates resistance to sliding of the protective tube (110) relative to the plunger (102). FIG. 23 illustrates a particular embodiment of an inserter (100), disposed with a longitudinal member (150) provided with a longitudinal rail (156). The cuff (116), attached to the proximal end of the protective tube (110) is slidably mounted over the rail. The cuff is provided with a tactile marker (117), which is a notch. The longitudinal member (150) is also provided with three tactile markers (153, 155, 157) which are notches. The practitioner is able to determine, both visually and by touch, when the respective markers are aligned. FIGS. 24 and 25 illustrates another particular embodiment of an inserter (100) that employs radial force, disposed with a longitudinal member (150) provided with a longitudinal guiding slot (151). The cuff (116), attached to the proximal end of the protective tube (110) is slidably mounted into the slot (151) by means of a T-rail (153).

The invention therefore provides an easy to use inserter (100), by which only a few simple steps are needed to prepare for insertion, to securely install and to position an intra-uterine device (120) into the uterus (200). Furthermore, the invention does not contain an abundance of separate and/or moving parts, thus reducing the costs for production. Since the invention uses frictional engagement rather than discrete stops, the protective tube (110) can be prevented from sliding relative to the plunger (102) at any desired position. This allows the inserter (100) to be used for the insertion of a wide range of IUD (120), without any significant structural changes to be made.

The handle (104) may have one of several different shapes and is designed for easy or comfortable handling of the inserter even when only using one hand. Preferably the handle (104) is shaped such that it lies comfortably in one hand, while the thumb and index finger of the same hand control the frictional engagement of the friction contact surface (152) against the protective tube (110). The handle may be hollow, optionally to house the discrete contact elements (170, 172, 174—FIGS. 25 to 28B) described elsewhere herein. The handle may be made from acrylanitrile butadiene styrene (ABS).

The plunger (102) attached to the handle (104), is preferably rigidly, and has a central longitudinal axis. It may be solid or hollow. It may have a groove or bore at least partially, optionally fully running in the longitudinal direction for holding the withdrawal string. Thus, the withdrawal string (130) is allowed to run or slide freely in it, reducing the risk of catching or snagging between the plunger (102) and the protective tube (110). The plunger (102) may have the shape of a longitudinal rod. The transverse cross section of the plunger (102) may have any suitable shape, for example, circular, oval, square, polygonal. The plunger (102) may be straight or curved so as to conform to the anatomy of the uterus (200).

The distal (30) tip of the inserter (100) may be made of a flexible material to avoid perforation of the uterus (200). The distal (30) tip of the plunger (102) is preferably smooth to avoid damage to the uterus (200). The distal (30) tip of the plunger (102) may be shaped to dismountably couple to the proximal (20) end of the central rod (124) of the IUD (120).

In a preferred embodiment of the invention, the plunger (102) and handle (104) form one piece. In a preferred embodiment of the invention, the plunger (102) and handle (104) are made from a single molding. This further reduces the production and assembly costs, since the inserter (100) can be cast from a single mold. This also reduces the risk of damage and/or breaking of the inserter (100).

Preferably, the plunger (102) and handle (104) are constructed from a biocompatible material or an inexpensive polymeric material, for example, resin, polycarbonate, polypropylene or a combination thereof. Said polymeric material may be relatively flexible as well as elastic to allow easy insertion of the plunger (102) into the cervical canal (220), and to provide a compliant member (spring) for the longitudinal member or members when incorporated, for example, into the tong-shaped gripping mechanism (106). On the other hand, said polymeric material requires sufficient rigidity to ensure correct placement of the IUD (120) into the uterus (200) and to ensure easy grip of the handle (104).

The total longitudinal length of the inserter (100) may be between 15 and 35 cm long. The plunger (102) may be between 10 and 30 cm long. The handle (104) may be between 1 and 5 cm wide. The handle (104), including longitudinal member (150) may be between 10 and 18 cm long. Preferably, the inserter (100) is between 20 and 30 cm long, more preferably between 27-29 cm long, the plunger (102) is between 15 and 25 cm long, more preferably between 21-23 cm long and the handle (104) is between 1.5 and 3 cm wide. The cuff, where present may be 5-10 cm long, preferable between 6-8 cm long; the length may include the slide member (178 FIGS. 25 to 28B) described elsewhere herein.

The plunger (102) may be at least partially, or entirely solid, i.e. there is no longitudinal lumen or groove. A solid design is cheaper to produce, stronger and avoids a difficult threading step of the inserting the withdrawal string (130) through the plunger lumen. Alternatively, it may have a groove or bore at least partially, optionally fully running in the longitudinal direction for holding the withdrawal string. According to a preferred embodiment of the invention, the plunger (102) is disposed with a longitudinal groove at least partly along the longitudinal length of the plunger (102), so providing the plunger (102) with a U-shaped cross-sectional profile. The longitudinal groove is preferably disposed along the full length of the plunger (102). The groove advances to the distal (30) tip of the plunger (102), which tip is shaped to dismountably couple to the proximal (20) end of the central rod (124) of the IUD (120). A suitable configuration for the distal tip may include an annular ring for receiving the proximal (20) end of the central rod (124) of the IUD (120) in the opening of the ring, whereby the opening of the ring is in connection with the longitudinal groove.

In an embodiment of the invention, the inserter (100) further comprises markings, optionally graduated, on the plunger (102), configured to identify optimal sliding positions of the protective tube (110) with respect to the plunger (102). These markings may assist in placing the IUD (120) at the correct depth of the uterus (200). The markings may be visual and/or tactile.

In an embodiment of the invention, the inserter (100) comprises one or more markings on the handle (104) or longitudinal member (150), optionally graduated, configured to identify optimal sliding positions of the protective tube (110) with respect to the plunger (102) or handle (104). At least one marking may assist in placing the protective tube (110) such that the wing tips of the IUD partially protrude (preferably are at least half out) from the tube (110) but are touching. The markings may be visual and/or tactile. Exemplary tactile markings (153, 155, 156) on the longitudinal member (150) are indicated in FIG. 23 which aligns with tactile markings (117) on the side of a cuff (116) when the cuff (116) is slidably moved.

In an embodiment of the invention, the surface of the plunger (102) is configured to provide a frictional grip on the protective tube (110). This allows for the protective tube (110) to be locked into its position relative to the plunger (102), without having to apply a strenuous force to the longitudinal member (150) (or tong-shaped gripping mechanism (106)). In a preferred embodiment, the inserter (100) comprises serrations on the surface of the plunger (102) configured to provide a frictional grip on the protective tube (110). The serrations are preferably a plurality of discrete horizontal bars.

In an embodiment of the invention, at least part of the surface of the longitudinal member (150) (or of the tong-shaped gripping mechanism) is configured to provide a frictional grip on the protective tube (110). This allows for the protective tube (110) to be locked into its position relative to the plunger (102), without having to apply a strenuous force to the longitudinal member (150) (or tong-shaped gripping mechanism (106)).

The friction contact surface (152) is typically disposed on a part of the surface of the longitudinal member facing the plunger (102). The friction contact surface may be provided towards the distal end of the longitudinal member (150). Alternatively, it may be along the length of the longitudinal member (150), for instance when it is a rail.

The friction contact surface (152) on the longitudinal member (150) may comprise serrations (154), configured to improve resistance to sliding of the protective tube (110) relative to the plunger (102) upon frictional engagement. The serrations are preferably a plurality of discrete horizontal bars.

The friction contact surface (152) may comprise a rubberized pad. Said pad preferably has a higher coefficient of friction compared with the other surface(s) of the longitudinal member. The rubberized pad is configured to improve resistance to sliding of the protective tube (110) relative to the plunger (102) upon frictional engagement.

The longitudinal member (150) is shorter than the plunger (102). The plunger (102) may extend distally beyond the distal end of the longitudinal member (150) by a distance equal to or greater than the depth of the uterus.

In an embodiment, the handle (106) may be further provided with a fastening means (108), also known as a fastening hook, configured to secure the withdrawal string (130), optionally under tension. This fastening means (108) allows for tension to be applied to the withdrawal string (130), keeping the IUD (120) into place (either wholly or partially covered by the protective tube (110)) during insertion into the cervical canal (220) and into the uterus (200). Preferably, this fastening means (108) is formed by a narrow slit (e.g. cleft) in the handle, as illustrated in FIG. 2. It is within the scope of the invention that the fastening means is absent.

In an embodiment of the current invention, the inserter (100) further comprises the protective tube (110) having a central lumen (hollow), through which the plunger (102) is disposed. The distal (30) end of the protective tube (110) is also configured for sliding over the intra-uterine device (IUD) (120). When over the IUD, the wings collapse or fold towards each other and the IUD is protected by the wall of the protective tube (110). A preferred embodiment of the protective tube (110) according to the present invention is illustrated in FIG. 5.

The protective tube (110) is preferably relatively stiff to provide sufficient pushability in the longitudinal direction. It is preferably non-elastic. It may be made from a relatively flexible material; it would still provide a stiff tube when in cylindrical form. The distal (30) end of the protective tube (110) may be rounded and smoothed to not harm the fundus (230) of the uterus (200).

In a preferred embodiment, the protective tube (110) is constructed from a polymeric material, such as polypropylene, polyethylene or polycarbonate.

In an embodiment, the protective tube (110) further comprises one or more markings, optionally graduated, configured to measure the position of the protective tube (110) with respect to the plunger (102). These markings may assist in placing the IUD (120) at the correct depth of the uterus (200). They may be used in conjunction with the collar or flange (114) mentioned below.

In an embodiment, the protective tube (110) further comprises one or more markings, optionally graduated, configured to measure the position of the protective tube (110) with respect to the longitudinal member (150). This is useful, for instance, to determine a position where the wings (122) of the IUD are covered by the protective tube (110) and the wing tips (126) of the IUD (120) partially protrude (preferably half are half out) from the protective tube (110) but are touching and the proximal (20) end of the IUD (120) is flush with the distal (30) end of the plunger (102).

In an embodiment of the present invention, the protective tube (110) further comprises a collar indicator, optionally sliding, configured to measure the position of the protective tube (110) with respect to the plunger (102). This sliding collar assists in placing the IUD (120) at the correct depth of the uterus (200).

In an embodiment of the present invention, the protective tube (110) further comprises a flange (114). A flange is a collar-like protrusion provided at a point along the outside surface of the protective tube (110). It may be slidable or non-slidable with respect to the protective tube (110). The slidable flange may be position-lockable. The flange (114) is configured such that contact between the flange (114) and the cervix (210) prohibits further insertion of the protective tube (110) into the uterine cavity (222). The protective tube (110) may further comprise one or more markings, optionally graduated, configured to measure the position of the flange (114) with respect to the distal end of the protective tube (110). The position of the flange (114) may be set based on a measurement of the uterus using a uterine sound. The flange (114) may be set to the depth of the uterus. The flange (114) may be set to prevent too-far advancement of the inserter (100) leading to perforation of the fundus (230) by the protective tube (110) or IUD (120). Preferably, the flange is set so that the distance between it and the distal end of the protective tube (110) is about equal to the depth of the uterus (as determined by a uterine sound, for instance), minus the length of the IUD wings (122).

In an embodiment of the present invention, the protective tube (110) further comprises a cuff (116) as shown, for instance, in FIG. 4. A cuff (116) is short collar disposed over the protective tube (116), typically as an overmolding. The cuff (116) is disposed at a point along the outside surface of the protective tube (110), most typically at the proximal end. It is generally fixed to the protective tube (110), and may be non-slidable with respect to it. The outer transverse profile of the cuff (116) may be essentially circular, essentially rectangular, or essentially square. The cuff (116) provides a surface for digital sliding of the protective tube (110), most in particular by the thumb. The cuff (116) may be configured to receive a force in a radial direction relative to the central longitudinal axis of the plunger (102), whereby the force is transferred to the longitudinal member (150), more in particular, to the friction contact surface (152) upon manual actuation of the cuff (116). The cuff is non-compressible in the radial direction, so that forces can be transmitted in the radial direction. It may be made from polypropylene, acrylanitrile butadiene styrene (ABS) or polyoxymethylene (POM).

The cuff (116) may further comprise one or more markings (117, FIG. 23)—visual and/or tactile—optionally graduated, configured to measure the position of the protective tube (110) with respect to the longitudinal member (150). One marking may indicate, for instance, a position where the wings (122) of the IUD are covered by the protective tube (110) and the wing tips (126) of the IUD (120) partially protrude (preferably half are half out) from the protective tube (110) but are touching and the proximal (20) end of the IUD (120) is flush with the distal (30) end of the plunger (102). Exemplary tactile marking on the side of a cuff (116) is indicated in FIG. 23, which aligns with tactile markings (152, 154, 156) on the longitudinal member (150) when the cuff (116) is slidably moved.

In an embodiment of the current invention, the friction contact surface (152) is comprised in a longitudinal guiding rail (156) as illustrated, for instance in FIGS. 4 and 23. Preferably, the protective tube is provided at the proximal (20) end with the aforementioned cuff (116), whereby the longitudinal guiding rail (156) and the cuff (116) are slidably connected. In a preferred embodiment of the current invention the longitudinal guiding rail (156) has a T-shaped profile and the cuff (116) has a reciprocating slot, through which slot the longitudinal guiding rail (156) can slide.

In an embodiment of the invention, the longitudinal member (150) comprises longitudinal guiding slot (151) as illustrated, for instance in FIGS. 24 and 24A. Preferably, the protective tube is provided at the proximal (20) end with the aforementioned cuff (116), whereby the longitudinal guiding slot (151) and the cuff (116) are engaged and slidably attached. In a preferred embodiment of the invention the cuff (116) is disposed with a T-shaped protrusion (153). The base of the T may be fixedly attached to the cuff (116). The longitudinal guiding slot (151) receives the T-shaped protrusion (153), thereby slidably attaching the cuff (116) to the longitudinal member (150). The cuff (116) and hence protective tube (110) are able to slide along the longitudinal guiding slot (151).

Figure 26:
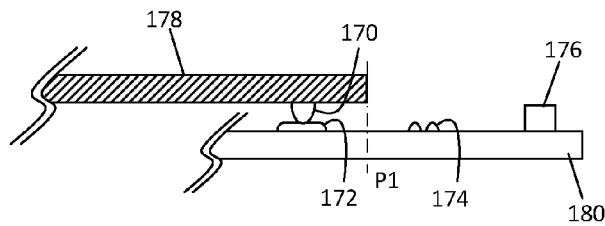
FIGS. 26 and 26A show an enlargement of the encircled area 171 of FIG. 25 which corresponding to configuration of the first and second discrete contact elements that position the protective tube relative to the plunger in a first discrete position.
Figure 26B:
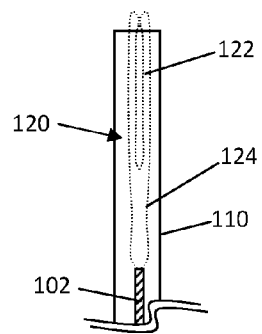
FIG. 26B depicts the IUD in the protective tube when the protective tube is positioned relative to the plunger in a first discrete position.

According to one embodiment and with reference to FIGS. 25 to 26B, the protective tube (110) is attached in fixed relation to a first discrete contact element (170) and the plunger is attached in fixed relation to a second discrete contact element (172), the first (170) and second (172) discrete contact elements being in slidable relation to each other and configured such that they frictionally engage together so increasing the resistance to sliding of the protective tube (110) relative to the plunger (102) selectively at a first discrete position (P1).

The first (170) and second (172) contact elements may be provided on separate slide members (178, 180) attached in fixed relation to the protective tube (110) and plunger (102) respectively. Accordingly, according to one embodiment, the protective tube (110) may be attached in fixed relation to a first slide member (178) and the plunger (102) may be attached in fixed relation to a second slide member (180), the first (178) and second (180) slide members being in slidable relation to each other, whereby a first sub-region of the first slide member is provided with the first discrete contact element (170) that can frictionally engage against the second sub-region of the second slide member provided with a second discrete contact element (172) so increasing the resistance to sliding of the protective tube (110) relative to the plunger (102) selectively at a first discrete position (P1).

Figure 26A:
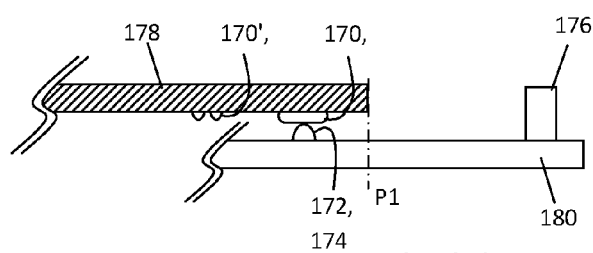

The first discrete contact element (170) attached in fixed relation to the protective tube (110), optionally via the first slide member (178), may be comprised in a protrusion (e.g. a pawl, finger), and the second discrete contact element (172) attached in fixed relation to the plunger (102), optionally via the second slide member (180), may be comprised in a discrete friction pad; this is illustrated, for example, in FIG. 26. Alternatively, the first discrete contact element (170) attached in fixed relation to the protective tube (110) optionally via the first slide member (178) may be comprised in a discrete friction pad, and the second discrete contact element (172) attached in fixed relation to the plunger (102) optionally via the second slide member (180) may be comprised in a protrusion (e.g. a pawl, finger); this is illustrated, for example, in FIG. 26A.

The first discrete position (P1) corresponds to a position of the protective tube (110) where it covers at least part of the wings (122) of the IUD (120) as illustrated, for example, in FIG. 26B. Preferably, P1 corresponds to a position of the protective tube (110) where it covers at least part of the wings (122) of the IUD (120), and the wings partially protrude from (preferably are half out of) the protective tube (110) but are touching when the central rod (124) of the IUD (120) is engaged with the distal (30) end of the plunger (102).

Figure 27:
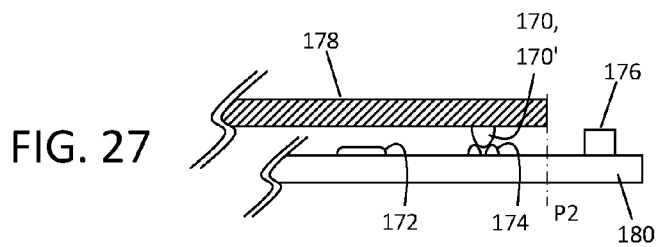
FIGS. 27 and 27A show an enlargement of the encircled area 171 of FIG. 25 which corresponding to configuration of the third and fourth discrete contact elements that position the protective tube relative to the plunger in a second discrete position.
Figure 27B:
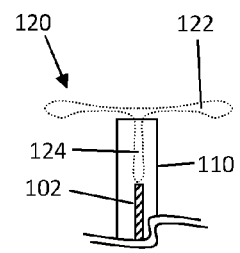
FIG. 27B depicts the IUD partially in the protective tube when the protective tube is positioned relative to the plunger in a second discrete position.

According to another embodiment and with reference to FIGS. 27 to 27B, the protective tube (110) is attached in fixed relation to a third discrete contact element (170') and the plunger is attached in fixed relation to a fourth discrete contact element (174), the third (170') and fourth (174) discrete contact elements being in slidable relation to each other and configured such that they engage together so increasing the resistance to sliding of the protective tube (110) relative to the plunger (102) selectively at a second discrete position (P2). According to one aspect, the first (170) and third (170') discrete contact elements are one and the same as indicated, for example, in FIG. 27.

The third (170') and fourth (174) contact elements may be provided on separate slide members (178, 180) attached in fixed relation to the protective tube (110) and plunger (102) respectively. The slide members (178, 180) may or may not be the same slide members on which the first (170) and second (172) contact elements are provided. According to one embodiment, a third sub-region of the first slide member is provided with the third discrete contact element (170') that can frictionally engage against the forth sub-region of the second slide member provided with a forth discrete contact element (174) so increasing the resistance to sliding of the protective tube (110) relative to the plunger (102) selectively at a second discrete position (P2). Preferably, the first (170) and third (170') sub-regions and hence discrete contact elements are one and the same as indicated, for instance, in FIG. 27.

The third discrete contact element (170') attached in fixed relation to the protective tube (110) may be comprised in a protrusion (e.g. a pawl, finger), and the fourth discrete contact element (174) attached in fixed relation to the plunger (102) may be comprised in a friction pad, or notch for receiving the protrusion as shown, for instance, in FIG. 27. The notch is preferably raised, relative, for example, to the slide member. It is understood that the first (170) and third discrete (170') contact elements may be one and the same; they may both be a protrusion (e.g. a pawl, finger).

Figure 27A:
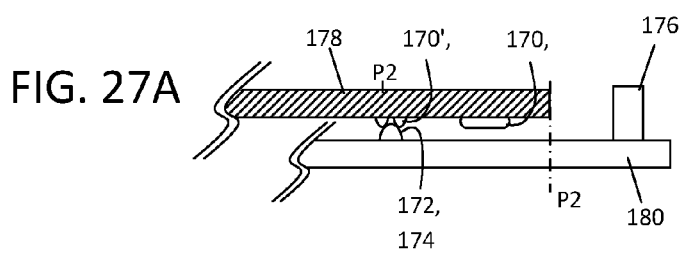

Alternatively, the third discrete contact element (170') attached in fixed relation to the protective tube (110) may be comprised in a friction pad or notch for receiving the protrusion, and the forth discrete contact element (174) attached in fixed relation to the plunger (102) may be comprised in a protrusion (e.g. a pawl, finger). The notch is preferably raised, relative, for example, to the slide member. It is understood that the second (172) and fourth (174) discrete contact elements may be one and the same; they may both be a protrusion (e.g. a pawl, finger); this is shown in FIG. 27A.

The second discrete position (P2) is spatially separated in a longitudinal direction from the first discrete position (P1). The second discrete position (P2) is proximal (20) to the first discrete position (P1). The second discrete contact element (172) may be spatially separated in a longitudinal direction from the fourth discrete contact element (174). The fourth discrete contact element (174) may be proximal to the second discrete contact element (172).

The second discrete position (P2) corresponds to a location of the protective tube (110) where it covers at least part of the IUD (120) central rod, and the wings are unfolded when the central rod (124) of the IUD (120) is engaged with the distal (30) end of the plunger (102), as illustrated, for instance, in FIG. 27B.

According to one embodiment, the protective tube (110) is attached in fixed relation to a fifth discrete contact element (170") and the plunger (102) is attached in fixed relation a sixth discrete contact element (176), the fifth discrete contact element (170") and sixth discrete contact element (176) being in slidable relation to each other and configured such that they engage, so limiting (stopping) the sliding of the protective tube (110) relative to the plunger (102) selectively at a third discrete position (P3).

The fifth contact element (170") and sixth contact element (176) may be provided on separate slide members (178, 180) attached in fixed relation to the protective tube (110) and plunger (102) respectively. The slide members may or may not be the same slide members on which the first (170) and second (172) discrete contact elements are respectively provided. According to one embodiment, a fifth sub-region of the first slide member is provided with the fifth discrete contact element (170") that can engage against a sixth sub-region of the second slide member provided with the sixth discrete contact element (176) so limiting (stopping) the sliding of the protective tube (110) relative to the plunger (102) selectively at a third discrete position (P3). The first (170), third (170') and fifth (170") sub-regions and hence discrete contact elements may be one and the same as shown, for instance, in FIG. 28.

The fifth discrete contact element (170") attached in fixed relation to the protective tube (110) may be comprised in a protrusion (e.g. a pawl, finger), and the sixth discrete contact element (176) attached in fixed relation to the plunger may be comprised in a stop member (e.g. a lug, protrusion). It is understood that the first (170), third (170'), and fifth (170") discrete contact elements may be one and the same; they may be a protrusion (e.g. a pawl, finger) as shown, for instance, in FIG. 28.

Alternatively, the fifth discrete contact element (170") attached in fixed relation to the protective tube may be comprised in a stop member (e.g. a lug, protrusion), and the fourth discrete contact element (176) attached in fixed relation to the plunger may be comprised in a protrusion (e.g. a pawl, finger). It is understood that the second (172), fourth (174), and sixth (176) discrete contact elements may be one and the same; they may be a protrusion (e.g. a pawl, finger) as shown, for instance, in FIG. 28B.

Figure 28:
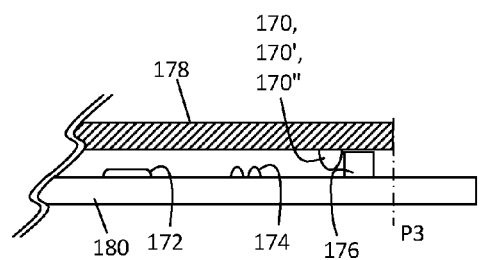
FIGS. 28, 28A and 28B depict an enlargement of the encircled area 171 of FIG. 25 which corresponding to configuration of the fifth and sixth discrete contact elements that position the protective tube relative to the plunger in a third discrete position.
Figure 28A:
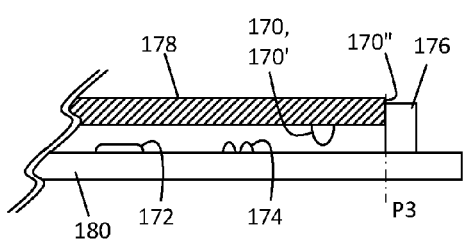

Alternatively, the fifth discrete contact element (170") attached in fixed relation to the protective tube (110) may be comprised in the proximal terminal end of the first slide member, and the sixth discrete contact element (176) attached in fixed relation to the plunger may be comprised in a stop member (e.g. a lug, protrusion), as shown, for instance, in FIG. 28A.

The third discrete position (P1) is spatially separated in a longitudinal direction from the second discrete position (P2) and from the first discrete position (P3). The third discrete position (P3) is proximal to the second (P2) and first (P1) discrete positions. The sixth contact element (176) is spatially separated in a longitudinal direction from the fourth contact element (174). The sixth contact element (176) is proximal to the fourth contact element (174).

Figure 28C:
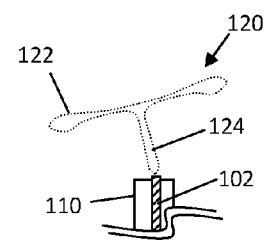
FIG. 28C depicts the IUD uncovered from the protective tube when the protective tube is positioned relative to the plunger in a third discrete position.
Figure 28B:
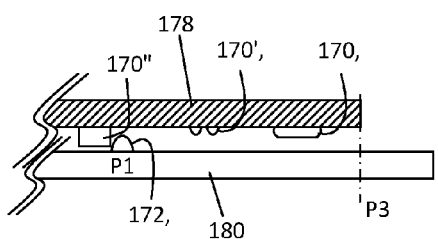

The third discrete position (P3) may correspond to a location of protective tube where IUD (120) central rod is uncovered when the central rod (124) of the IUD (120) is engaged with the distal (30) end of the plunger (102), as illustrated, for instance, in FIG. 28C.

The slide members are preferably longitudinal elements, arranged to slide relative to each other. The respective longitudinal members may be aligned in essentially parallel orientation.

The first slide member (178), attached in fixed relation to the protective tube (110), is preferably a longitudinal element. The first slide member (178) may be attached to the cuff (116) or to the protective tube (110). The first slide (178)

member may be disposed proximal to the proximal end (20) of the protective tube (110) or to the cuff (116).

The second slide member (180), attached in fixed relation to the handle (104), is preferably a longitudinal element. The second slide member (180) may be integrated into the handle (104). The first slide member may be disposed proximal to the proximal end (20) of the plunger (102).

A discrete contact element refers to a structure adapted for contact with another discrete contact element. When the discrete contact elements contact each other, there may be a resistance to movement. The resistance to movement may be caused, for instance, by friction, by the force of magnetism, by a notch and groove which provides indexed movement, or by a stop member which limits movement.

The discrete friction pad that may be comprised in a discrete contact element may comprise serrations, configured to improve resistance to sliding of the protective tube (110) relative to the plunger (102) upon frictional engagement. The serrations are preferably a plurality of discrete horizontal bars or a plurality of bumps.

The discrete friction pad that may be comprised in a discrete contact element may comprise a rubberized pad. Said pad preferably has a higher coefficient of friction compared with the other surface(s). The rubberized pad is configured to improve resistance to sliding of the protective tube (110) relative to the plunger (102) upon frictional engagement.

The other discrete contact elements besides the discrete friction pad e.g. the protrusion, pawl and notch may be made from the same material as the handle when they are disposed in fixed relation to the handle e.g. from acrylanitrile butadiene styrene (ABS). Alternatively, they may be made from the same material as the cuff when they are disposed in fixed relation to the plunger e.g. from ABS (acrylanitrile butadiene styrene) or POM (polyoxymethylene).

Figure 29:
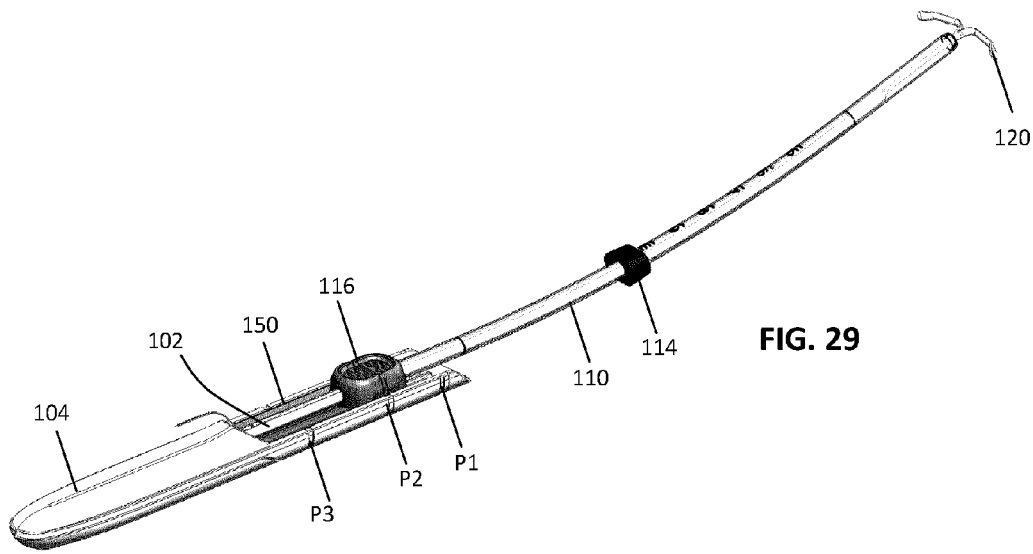
FIG. 29 depicts a perspective view of an inserter provided with a sliding cuff and handle in which a plurality of discrete contact elements is housed.
Figure 30:
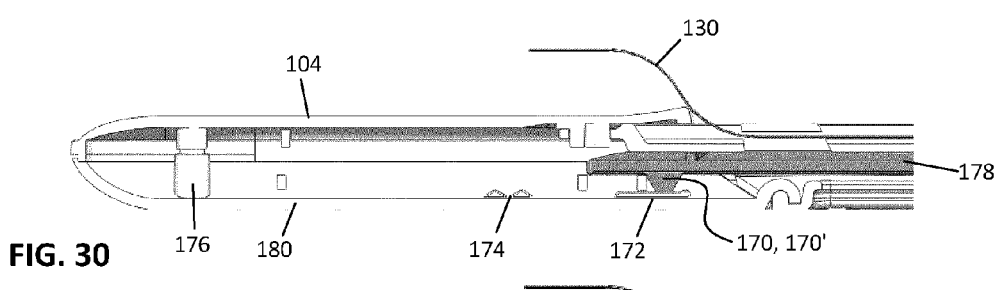
FIG. 30 shows a cross-sectional view of the inserter handle where the protective tube is positioned relative to the plunger at a first discrete position.
Figure 31:
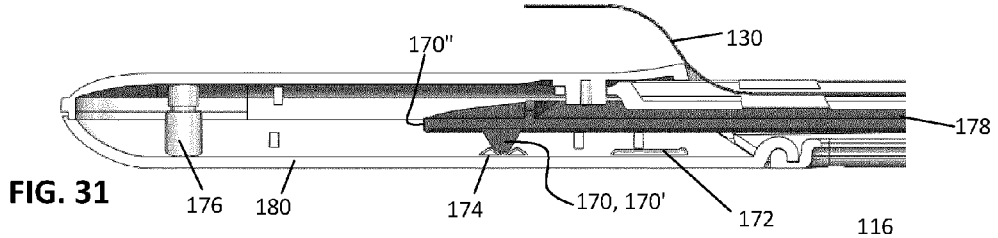
FIG. 31 shows a cross-sectional view of the inserter handle where the protective tube is positioned relative to the plunger at a second discrete position.
Figure 32:
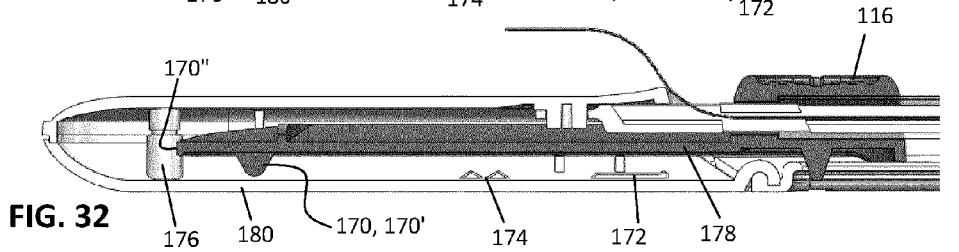
FIG. 32 shows a cross-sectional view of the inserter handle where the protective tube is positioned relative to the plunger at a third discrete position.

Preferable, an inserter (100) comprises the aforementioned first, second, third, fourth, fifth and sixth discrete contact elements, wherein the first, third and fifth discrete contact elements are one and the same, and comprised in a protrusion (e.g. pawl, finger), and the second, fourth and sixth discrete contact elements are separate and spatially separated. Preferably, the protective tube (110) is provided with one or markings, preferably the protective tube (110) is provided with a flange (114), and preferably the plunger (102) is provided with a longitudinal groove. Preferably the handle (104) and longitudinal member (150) are made from the same material, more preferably are made from ABS (acrylanitrile butadiene styrene). An example of such an inserter is provided in FIGS. 29 to 32. FIG. 29 depicts an inserter disposed with a handle (104) extended by a longitudinal member (150) and attached to a plunger (102). The protective tube (110) is provided with a flange (114) and is attached to a cuff (116). Notches on the side of the longitudinal member (150) correspond to discrete positions one (P1), two (P2) and three (P3). FIG. 30 depicts a cross-section of the handle (104) of FIG. 29 where the protective tube and plunger are in the first discrete position, and the first contact element (170, a pawl) and the second discrete contact element (172, a friction pad) are frictionally engaged. FIG. 31 depicts a cross-section of the handle (104) of FIG. 29 where the protective tube and plunger are in the second discrete position, and the first and third contact elements are one and the same (170, 170', a pawl) are engaged with the fourth discrete contact element (174, a raised notch). FIG. 32 depicts a cross-section of the handle (104) of FIG. 29 where the protective tube and plunger are in the third discrete position, and the fifth contact element (170", a distal terminal end) is engaged with the sixth discrete contact element (176, a lug).

The inserter (100) according to the invention is particularly suitable for the positioning of T-shaped intra-uterine devices. However, it is also applicable to other types of IUDs having different sizes and shapes, as long as these can be managed to enter the protective tube by appropriate arrangements. The inserter could thus also be suitable for installing intra-uterine devices having a flexible frame with continuous curved shape, for example circular, oval, spiral, toroidal, triangular, shield-like, almond-like, diamond-like, elliptical or polygonal shape.

In an embodiment of the current invention, the inserter (100) further comprises a T-shaped intra-uterine device (IUD) (120). An IUD comprises a pair of wings (122) fixed to a central rod (124). The wings (122) are diametrically opposed with respect to the central axis of the central rod (124). In an embodiment of the invention, the wings (122) of the intra-uterine device (IUD) (120) comprise wing tips (126)—also known as hands. The tips at the end of these wings may be rounded off. The central rod and the wings form a substantially T-shaped piece when the device is positioned in the uterus. In addition to a T-shape, IUDs also exist in other shapes such as a ring, a rod, a '7' or an 'S'. The intra-uterine device (IUD) (120) is positioned at the distal (30) end of the plunger (102). The IUD may be dismountably connected to the distal (30) tip of the plunger (102).

In an embodiment of the invention, the central rod (124) of the IUD (120) is protected by placement of the protective tube (110) that at least partially covers the IUD (120) during packaging and transport of the device.

In an embodiment, the intra-uterine device (IUD) (120) is coated or impregnated with a medicament. Said medicament can be a drug or a hormone, such as levonorgestrel, or any other active agent. Said medicament can aid the use of the IUD for contraception, or can reduce menorrhagia in women. Said medicament can also serve other purposes.

In an embodiment, the intra-uterine device (IUD) (120) is partially or wholly constructed from a biocompatible material, a polymeric material (polyethylene in particular), copper, gold, silver or a combination thereof. Furthermore, the intra-uterine device (120) can have a coating or surrounding wiring in one of these materials. These materials can be inert with respect to the uterus (200), or they can secrete ions that have a contraceptive or medicinal effect.

In an embodiment, the intra-uterine device (IUD) (120) is configured as a method of contraception or as a treatment for menorrhagia.

In a preferred embodiment, the wings (122) of the IUD (120) are configured to fold or unfold responsive to the slidable movement of a protective tube (110) that can cover or uncover the wings (122) of the IUD (120).

The IUD may further comprise a withdrawal string (130) attached at one end, preferably to the rod (124). The withdrawal string (130) comprises a proximal (20) end and a distal (30) end.

After insertion of an IUD (120), the withdrawal string (130) remains positioned within the cervix (210) for a period of up to 5 to 10 years to facilitate extraction of the IUD (120) by the health care provider. The withdrawal string (130) also allows the patient to check whether the IUD (120) is still correctly in place. The term 'string' in this application also refers to a withdrawal string (130) consisting of one or multiple strands.

A preferred embodiment of a T-shaped IUD (120) attached to a withdrawal string (130) is illustrated in FIG. 7.

In a preferred embodiment, the withdrawal string (130) passes through the protective tube (110) from the distal (30) end to the proximal (20) end, as illustrated in FIG. 8, more in particular, through the central lumen of the protective tube (110).

In an embodiment, the withdrawal string (130) is constructed from a polyamide or fishing line material.

In a preferred embodiment, the inserter (100) is configured such that tension applied to the withdrawal string (130) maintains the IUD (120) in contact with the distal (30) end of the plunger (100) while the protective tube is advanced at least partially over the IUD. This ensures that the IUD (120) remains optimally positioned during the insertion process.

A proximal (20) end of the withdrawal string (130) may be permanently fixed to the handle (104), and under tension to maintain the IUD (120) in contact with the distal (30) end of the plunger (102). The tension would be released by cutting the string (130).

The withdrawal string (130) attached to the IUD (120) may be immobilized by the fastening means (108) on the handle (104) of the inserter (100), to keep the IUD (120) at a steady and correct position in the uterus (200). The tension would be released by detaching the string from the fastening means (130).

The inserter (100) may be provided together with protective tube (110) disposed over the plunger, with the IUD (120) at the distal end of the plunger (102), and with the withdrawal string (130) disposed within the lumen of the protective tube (110). The combination is known as an inserter assembly (160), as shown, for instance, in FIGS. 8 to 15. The inserter assembly has corresponding distal (30) and proximal (20) ends. The inserter assembly may be supplied pre-packaged. The packaging seals the inserter assembly against contamination from micro-organisms. The package may be peelably opened. The inserter assembly may be supplied with the string of the IUD (120) under tension such that the central rod of the IUD is engaged with the distal tip of the plunger (102). Alternatively, the IUD (120) may be supplied without the string under tension.

Prior to use, the IUD (120) is preferably positioned inside the distal end of the hollow of the protective tube (110) wherein the wings (122) of the IUD are covered by the protective tube (110) and the wing tips (126) of the IUD (120) partially protrude (preferably are half out) from the protective tube (110) but are touching and the proximal (20) end of the IUD (120) is engaged with the distal (30) end of the plunger (102). This is known as a primed position. The inserter assembly may be supplied with the IUD (120) already primed, or with the IUD (120) positioned fully or partially outside the protective tube (110) to be manually primed prior to use.

With reference to FIGS. 8 to 11 inserter assembly may be primed by a method comprising the following steps:
 a) keeping the withdrawal string (130) relaxed (i.e. tension not applied, FIG. 8);
 b) advancing (FIG. 9) partially the protective tube (110) distally over the plunger (102) (which concomitantly advances the opened IUD (120)) until the protective tube (110) is positioned such that the wing tips of the IUD (120) would partially protrude from (preferably are half out of) the protective tube (110) but are touching when the central rod of the IUD (120) is engaged with the distal (30) end of the plunger (102);
 c) activating (FIG. 10) frictional engagement of the friction contact surface (152) against the protective tube (110), so as to fix the position of the protective tube (110) relative to the plunger (102); and
 d) providing tension (FIG. 10) to the withdrawal string (130), wherein the IUD (120) enters inside the hollow of the protective tube (110) until (FIG. 11) the wings (122) of the IUD are covered by the protective tube (110) and the wing tips (126) of the IUD (120) partially protrude (preferably are half out) from the protective tube (110) but are touching, and the proximal (20) end of the IUD (120) is engaged with the distal (30) end of the plunger (102);
 e) thereby priming the inserter assembly.

The position of the protective tube (110) in step b) may be determined using visual or tactile markings on the protective tube (110), and/or handle, and/or plunger (102). Tension on the string (130) may be released or maintained prior to insertion.

With reference to FIGS. 12 to 15, the inserter assembly (160) may be primed by an alternative method comprising the following steps:
 a) placing (FIG. 12, FIG. 13) the withdrawal string (130) under tension (e.g. fixing to the handle) so that the proximal (20) end of the IUD (120) is engaged with the distal (30) end of the plunger (102); and
 b) partially advancing (FIG. 14) the protective tube (110) and IUD (120) forward until (FIG. 15) the wings (122) of the IUD are covered by the protective tube (110) and the wing tips (126) of the IUD (120) partially protrude (preferably are half out) from the protective tube (110) but are touching;
 c) thereby priming the inserter assembly (160).

The steps are performed without activating frictional engagement of the friction contact surface (152) against the protective tube (110), so that the protective tube (110) can slide relative to the plunger (102). Tension on the string (130) may be released or maintained prior to insertion.

Figures 33, 34:
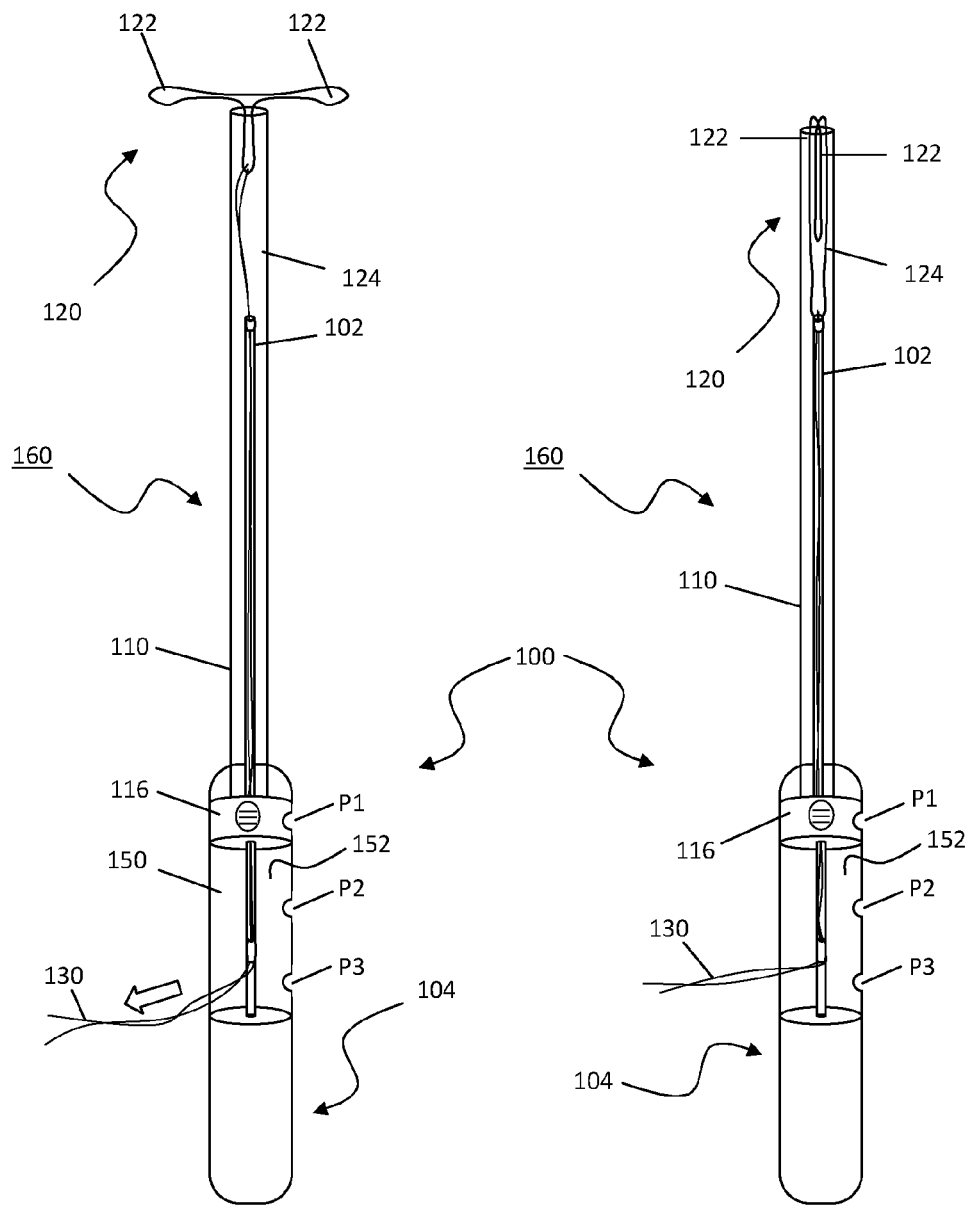
FIGS. 33 and 34 show a perspective view of an inserter assembly where the protective tube is positioned relative to the plunger at a first discrete position, and possible steps of priming using this inserter.
Figure 35:
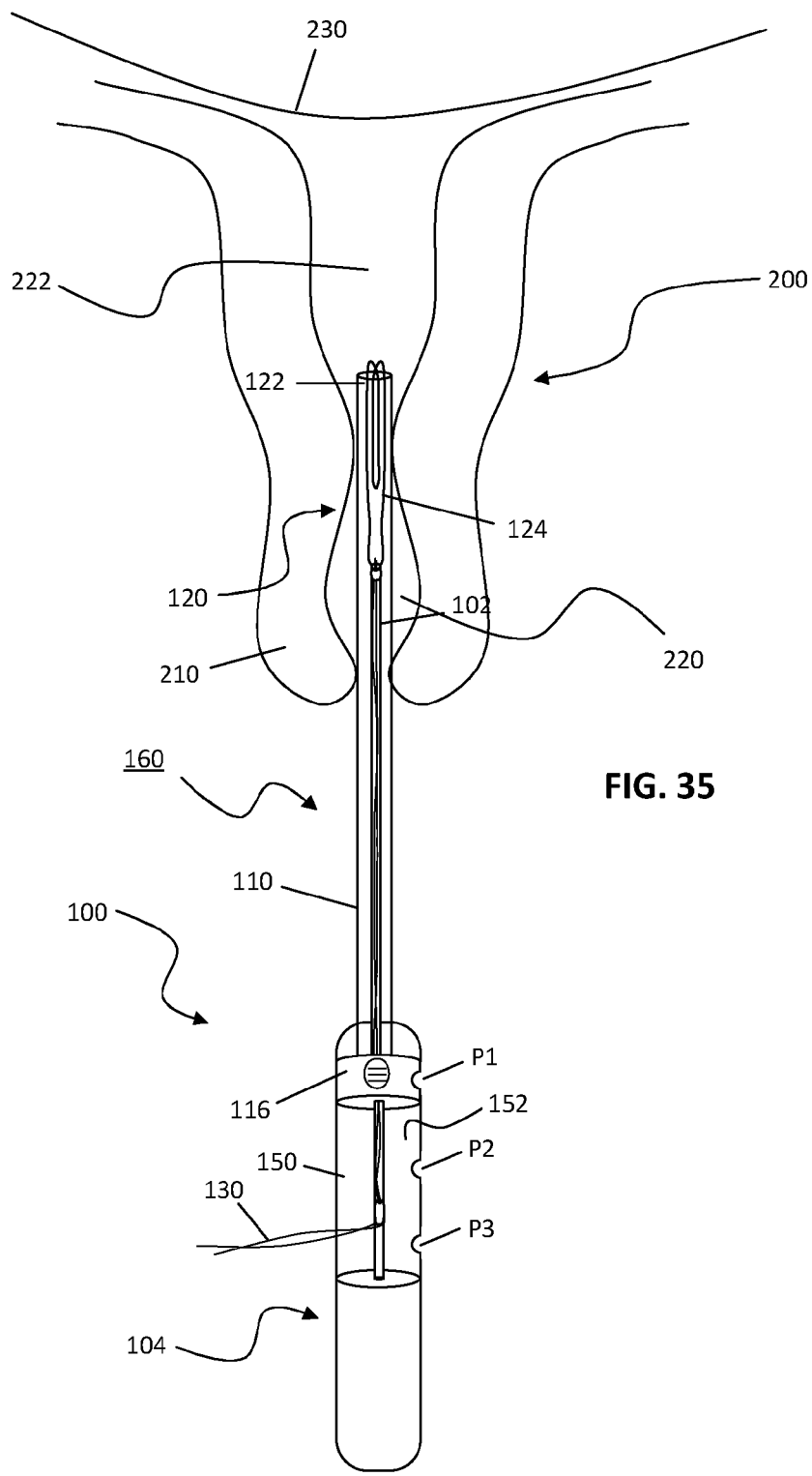
FIGS. 35 to 38 provide a schematic illustration of steps of a method for inserting an IUD (120) attached to a withdrawal string (130) using a embodiment of the inserter device (100) and a protective tube (110) disposed with discrete contact elements, comprising various steps according to a preferred embodiment of the invention.
Figure 36:
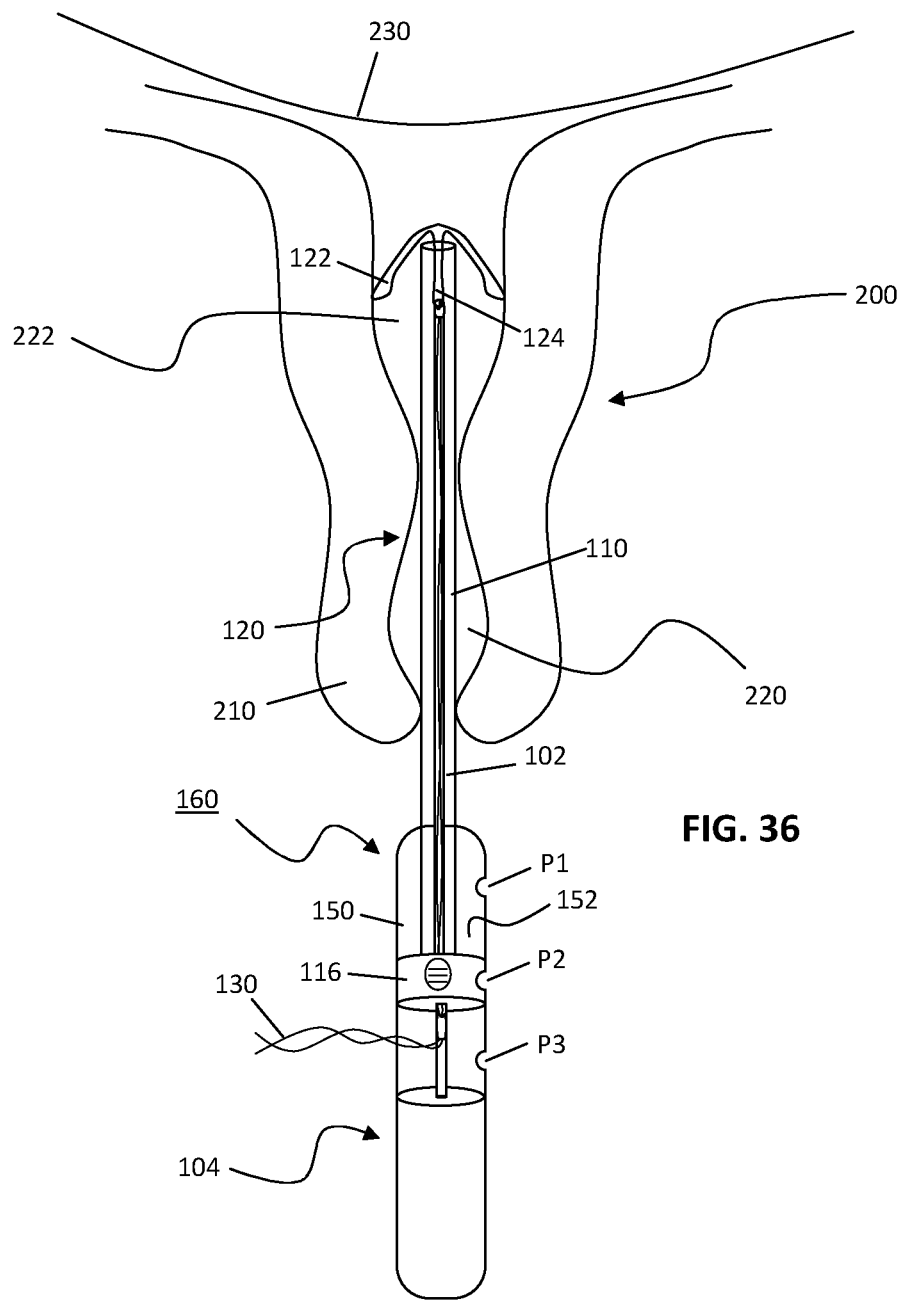
Figure 37:
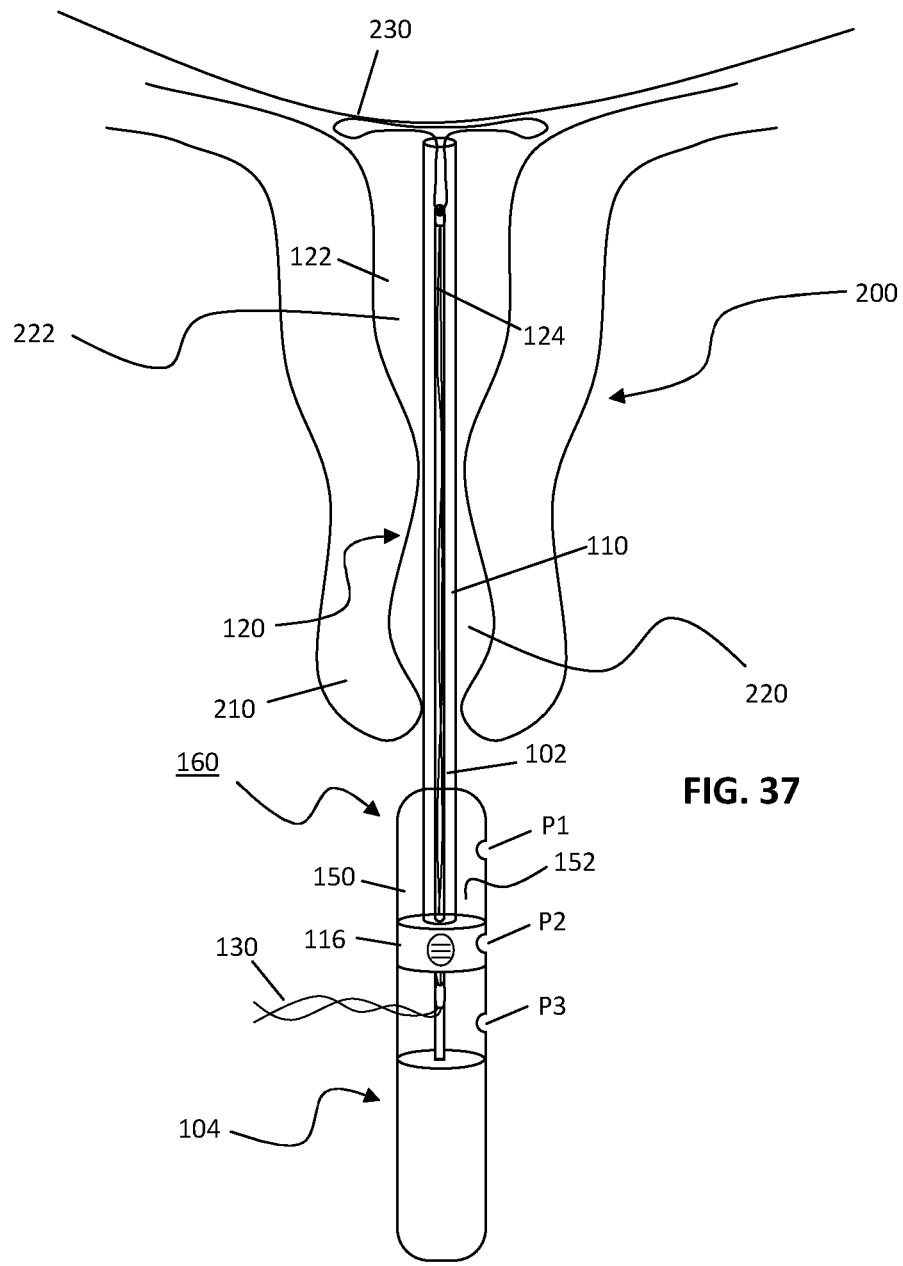
Figure 38:
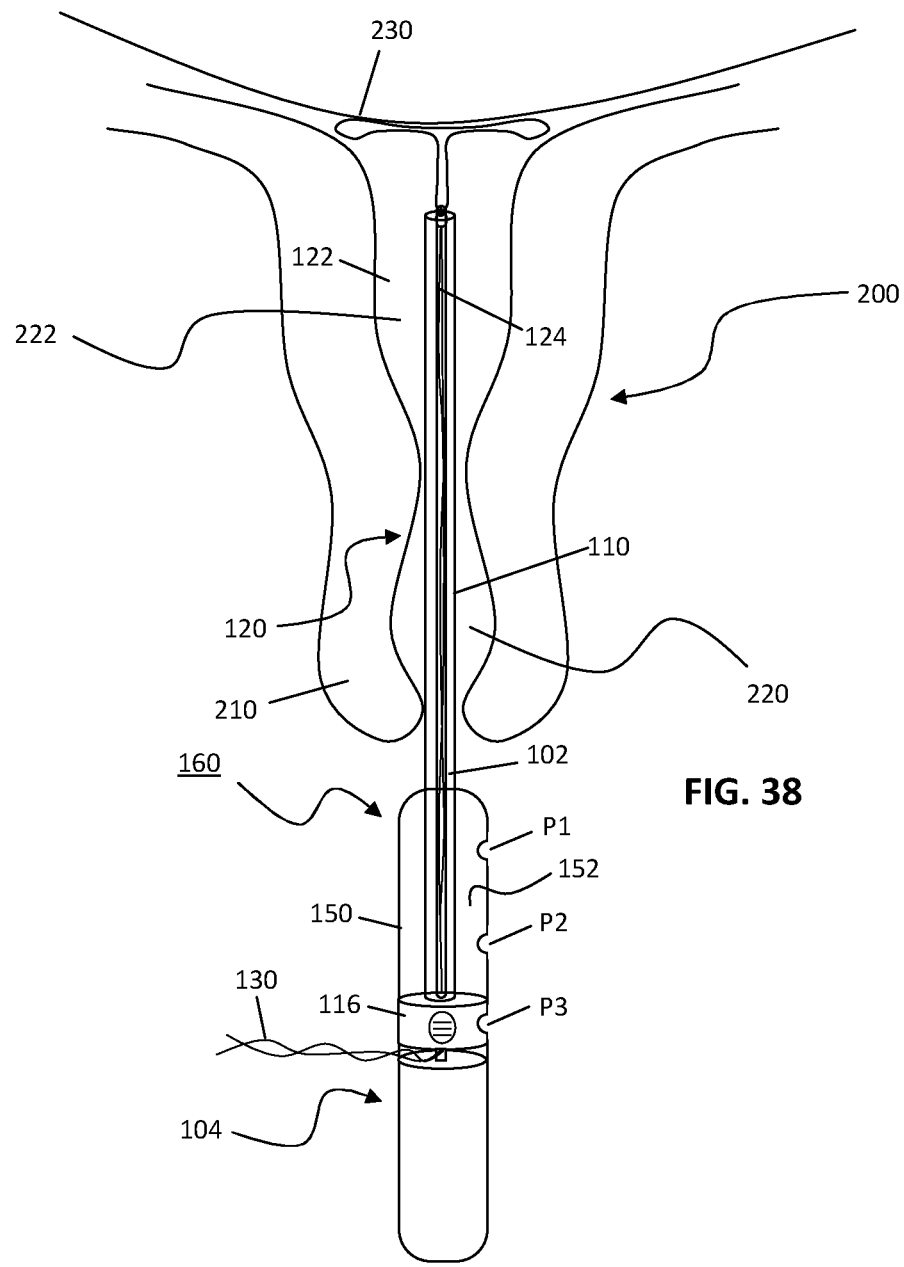

With reference to FIGS. 33 to 34, the inserter assembly (160) may be primed by a further alternative method comprising the following steps:
 a) partially advancing (FIG. 33) the protective tube (110) and IUD (120) forward by sliding the cuff (116) until the first discrete position (P1) is reached (FIG. 33), and activating frictional engagement of the cuff (116) against the friction contact surface (152) of the longitudinal member (150)
 b) placing (FIG. 33, 34) the withdrawal string (130) under tension so that the proximal (20) end of the IUD (120) engaged with the distal (30) end of the plunger (102); and the wings (122) of the IUD are covered by the protective tube (110) and the wing tips (126) of the IUD (120) partially protrude (preferably are half out) from the protective tube (110) but are touching;
 c) thereby priming the inserter assembly (160).

Tension on the string (130) may be released or maintained prior to insertion.

The invention also relates to a method for inserting and positioning the IUD (120) by use of the inserter assembly.

The inserter assembly may have been previously primed with an IUD (120) such that the wings (122) of the IUD (120) are covered by the protective tube (110) and the wing tips (126) of the IUD (120) partially protrude (preferably are half out) from the protective tube (110) but are touching. The inserter assembly may have been primed using one of the methods described herein. With reference to FIGS. 16 to 23 one method for inserting the IUD (120) using an inserter assembly of the invention comprises the steps:

a) activating frictional engagement of the friction contact surface (152) against the protective tube (110), so as to fix the position of the protective tube (110) relative to the plunger (102);
b) advancing (FIG. 16) the distal end of the inserter assembly through the cervical canal (220) and partially into the uterine cavity (222);
c) releasing (FIG. 17) frictional engagement of the friction contact surface (152) against the protective tube (110);
d) withdrawing (FIG. 17) the protective tube (110), such that the wings (122) of the IUD (120) are uncovered from the protective tube (110), but the central rod (124) remains covered by the protective tube (110);
e) activating (FIG. 18) frictional engagement of the friction contact surface (152) against the protective tube (110), so as to fix the position of the protective tube (110) relative to the plunger (102);
f) advancing (FIG. 18) further the distal end of the inserter assembly into the uterine cavity (222); and
g) withdrawing the inserter (100) and withdrawing the protective tube (110), simultaneously (FIG. 19) or sequentially (FIG. 20, FIG. 21);
h) thereby inserting and positioning the IUD (120).

Figure 16:
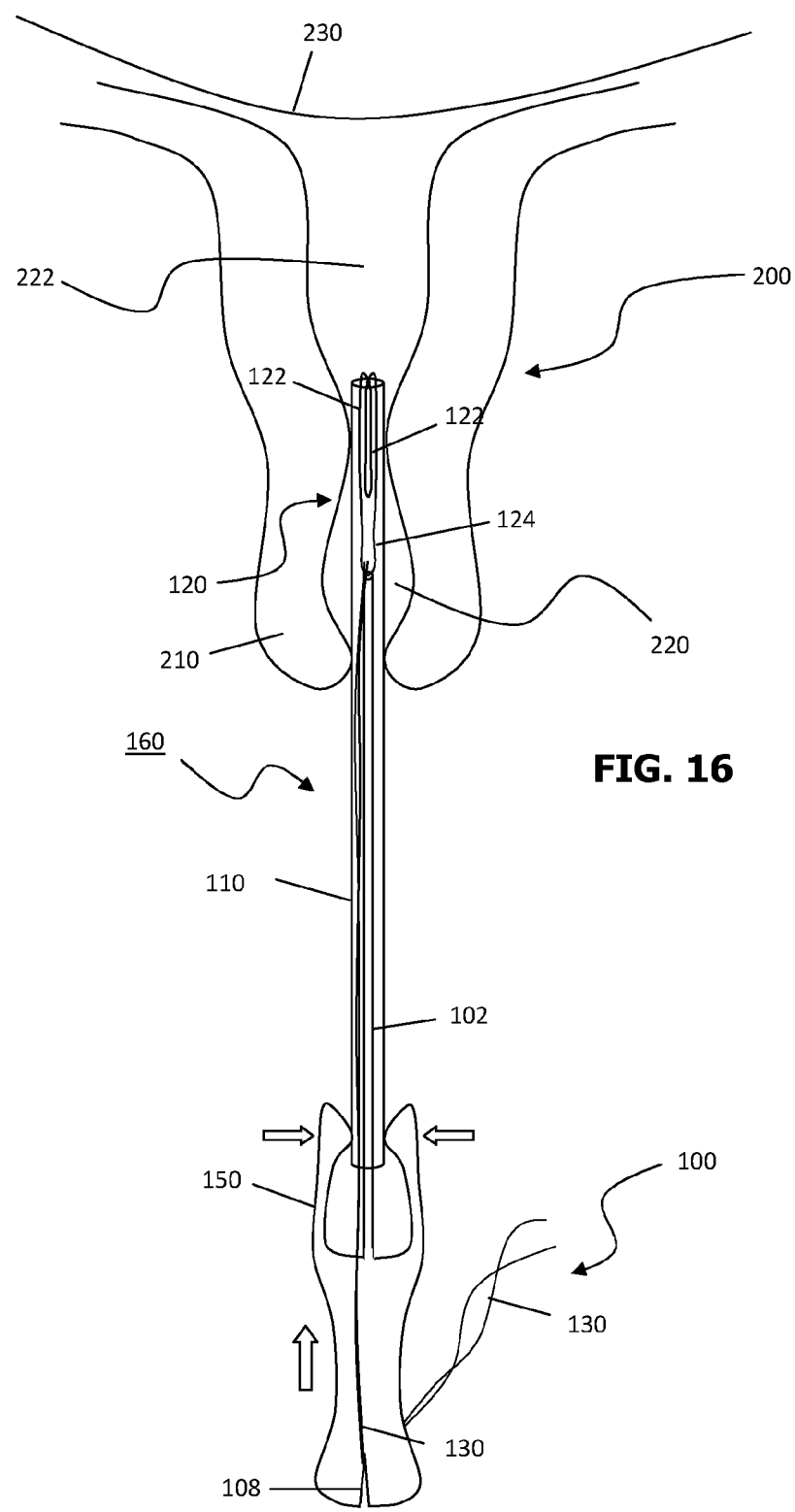
FIGS. 16 to 22 provide a schematic illustration of steps of a method for inserting an IUD (120) attached to a withdrawal string (130) using an embodiment of the inserter device (100) and a protective tube (110), comprising various steps according to a preferred embodiment of the invention.
Figure 17:
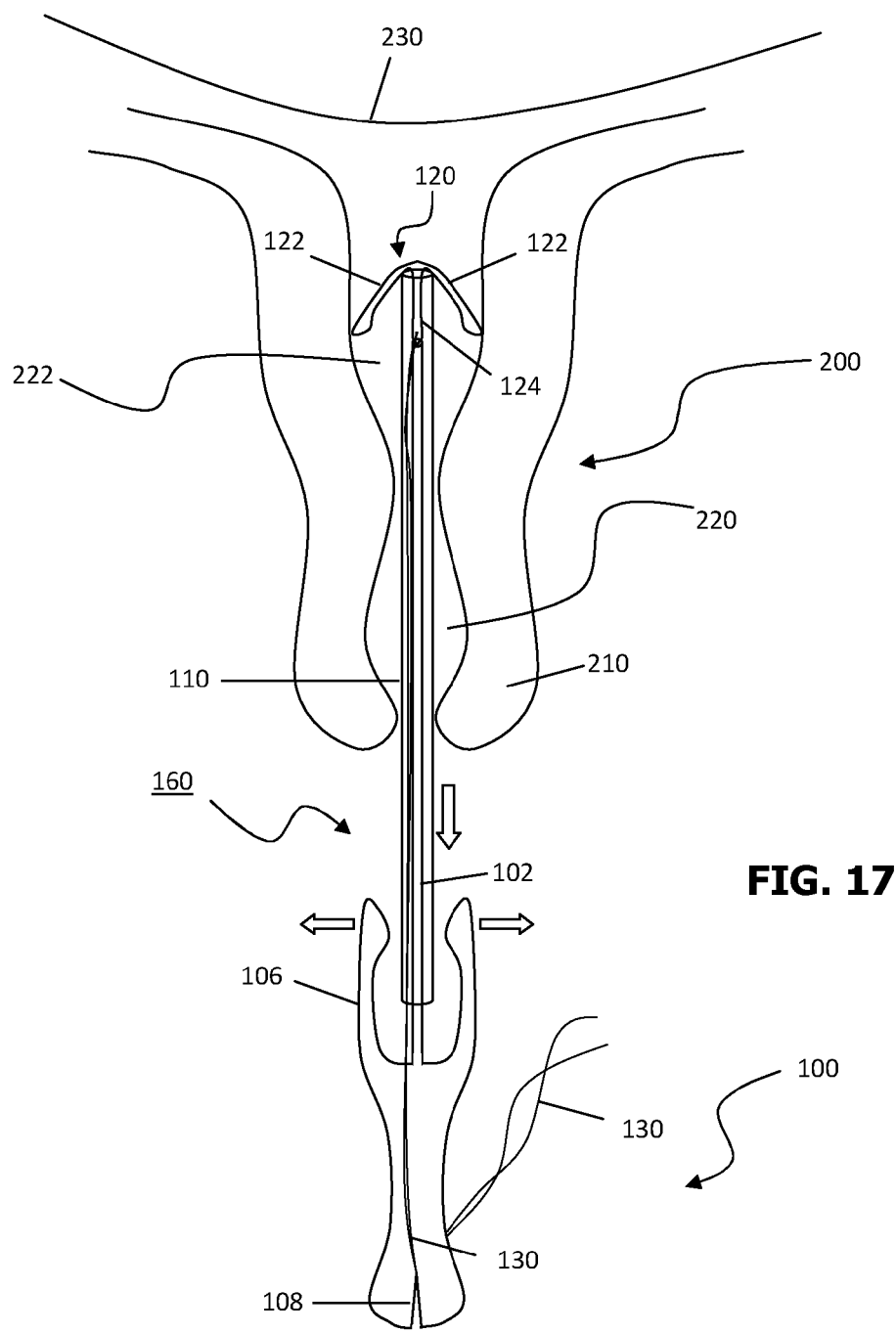
Figure 18:
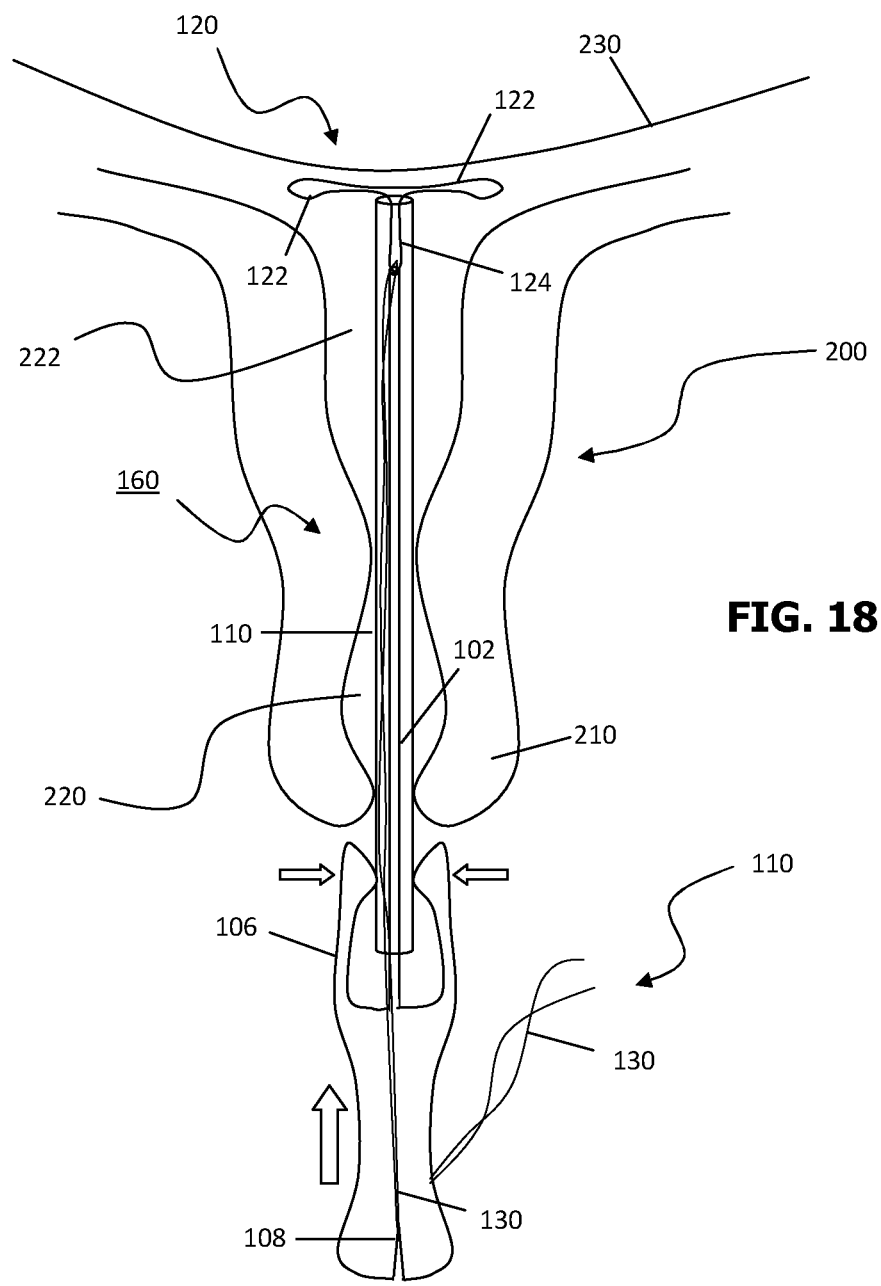

In step b), the inserter assembly may be advanced until the distal tip of the protective tube (110) has reached a midsection in the uterine cavity (222). In step f), the inserter assembly may be advanced until the opened IUD (120) has reached the fundus (230). To facilitate placement in steps b) and f), the protective tube (110) of the inserter assembly may be provided with a flange (114) described elsewhere herein. When the flange (114) contacts with the wall of the entrance to the cervix (210) in step b), it acts as a stop indicating that the distal tip of the protective tube (110) has reached a midsection in the uterine cavity (222). When the flange (114) contacts the wall of the entrance to the cervix (210) in step f), it acts as a stop indicating that the IUD (120) has reached the fundus (230). FIGS. 16, 17, and 18 show the string (130) under tension during insertion, however this is optional. Between steps b) and c), tension on the withdrawal string (130) may be released if the string is under tension; the string may thereafter be secured without tension, to the fastening means (108) or held under the thumb or finger to prevent entanglement. Between steps f) and g), where the string is still under tension, or where the string has been secured to the fastening means (108) or held to prevent entanglement, it may be fully released.

Figure 21:
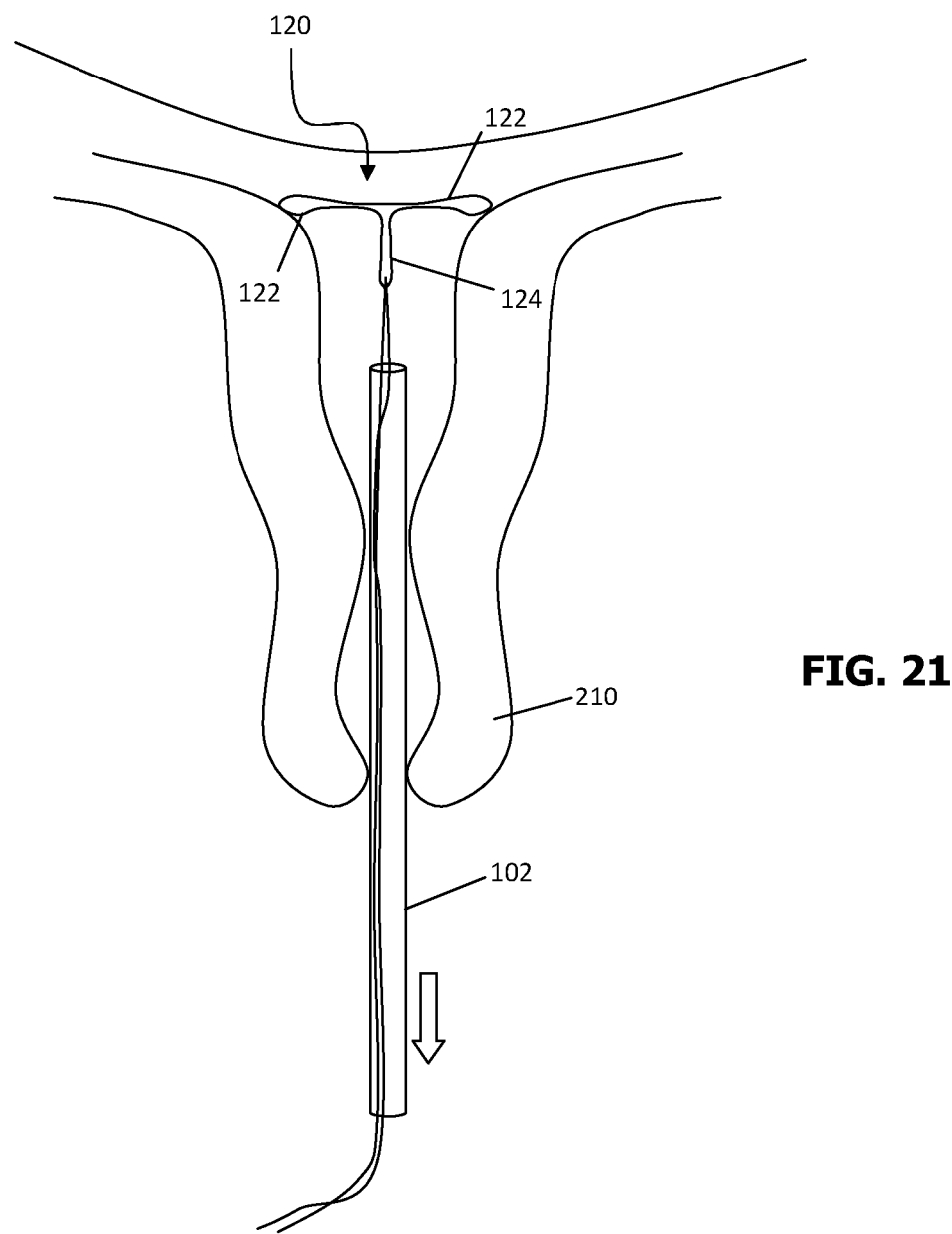

In regard of step g), when the inserter (100) and protective tube (110) are withdrawn simultaneously (FIG. 19), frictional engagement of the friction contact surface (152) against the protective tube (110) is maintained, so as to fix the position of the protective tube (110) relative to the plunger (102). In regard of step g), when the inserter (100) and withdrawing the protective tube (110) are withdrawn sequentially, frictional engagement of the friction contact surface (152) against the protective tube (110) is released (FIG. 20), then the inserter (100) is withdrawn (FIG. 20), followed by withdrawal of the protective tube (FIG. 21).

With reference to FIGS. 35 to 38 an alternative method for inserting the IUD (120) using an inserter assembly of the invention comprises the steps:
a) activating frictional engagement of the cuff (116) of the protective tube (110) against the friction contact surface (152) in the first discrete position (P1), so as to fix the position of the protective tube (110) relative to the plunger (102);
b) advancing (FIG. 35) the distal end of the inserter assembly through the cervical canal (220) and partially into the uterine cavity (222);
c) releasing (FIG. 36) frictional engagement of the cuff (116) of the protective tube (110) from the friction contact surface (152);
d) retracting the (FIG. 36) the protective tube (110) by sliding the cuff (116) to the second discrete position (P2), so that the wings (122) of the IUD (120) are uncovered from the protective tube (110), but the central rod (124) remains covered by the protective tube (110);
e) activating (FIG. 36) frictional engagement of the cuff (116) of the protective tube (110) against the friction contact surface (152), so as to fix the position of the protective tube (110) relative to the plunger (102) in the second discrete position (P2);
f) advancing (FIG. 37) further the distal end of the inserter assembly into the uterine cavity (222); and
g) releasing (FIG. 37) frictional engagement of the cuff (116) of the protective tube (110) from the friction contact surface (152);
h) retracting the (FIG. 38) the protective tube (110) by sliding the cuff (116) to the third discrete position (P3), so that the central rod (124) is uncovered from the protective tube (110);
g) withdrawing the inserter (100);
h) thereby inserting and positioning the IUD (120).

In step b), the inserter assembly may be advanced until the distal tip of the protective tube (110) has reached a midsection in the uterine cavity (222). In step f), the inserter assembly may be advanced until the opened IUD (120) has reached the fundus (230). To facilitate placement in steps b) and f), the protective tube (110) of the inserter assembly may be provided with a flange (114) described elsewhere herein. When the flange (114) contacts with the wall of the entrance to the cervix (210) in step b), it acts as a stop indicating that the distal tip of the protective tube (110) has reached a midsection in the uterine cavity (222). When the flange (114) contacts the wall of the entrance to the cervix (210) in step f), it acts as a stop indicating that the IUD (120) has reached the fundus (230). In regard of step g), the inserter (100) and protective tube (110) are withdrawn simultaneously.

The following describes a further alternative method for inserting and positioning an intra-uterine device (IUD) (120) by use of an inserter (100) as described above wherein the longitudinal member (150) comprises a gripping mechanism. Said method comprising the following steps:
a) covering the IUD (120) with the protective tube (110), while keeping the withdrawal string (130) relaxed;
b) partially advancing the inserter (100) into the cervical canal (220), while activating the gripping mechanism (106), while keeping the withdrawal string (130) under tension;
c) partially withdrawing the protective tube (110), while de-activating the gripping mechanism (106), while keeping the withdrawal string (130) under tension, such that the wings (122) of the IUD (120) unfold and are uncovered from the protective tube (110);
d) fully advancing the inserter (100) into the cervical canal (220), while activating the gripping mechanism (106), while keeping the withdrawal string (130) under tension; and
e) fully withdrawing the inserter (100), while activating the gripping mechanism. (106), while releasing the tension on the withdrawal string (130).

A more detailed explanation for priming, inserting and positioning the T-shaped intra-uterine device (120) is given hereafter with reference a specific example and to FIGS. 13 to 19. The following procedure may be utilised.

Figure 12:
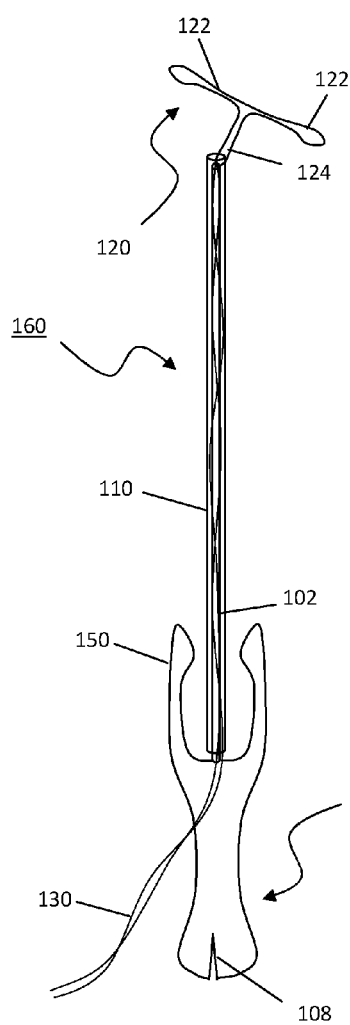

To prepare for the insertion, the sterile package is carefully opened. The IUD (120) is already in a correct configuration relative to the inserter as shown in FIGS. 8 and 12 and there is no need to align the intra-uterine device (120) or to thread the withdrawal string (130) through the protective tube (110). The IUD (120) is positioned at the distal (30) end of the plunger. In the configuration as packaged shown in FIGS. 8 and 12, the withdrawal string (130) is relaxed (i.e. not under tension from the fastening means (108)), the protective tube (110) is fully retracted over the plunger (102) and the friction contact surface (152) is not engaged against the protective tube (110); in other words the tong-shaped gripping mechanism (106) is relaxed.

Figure 13:
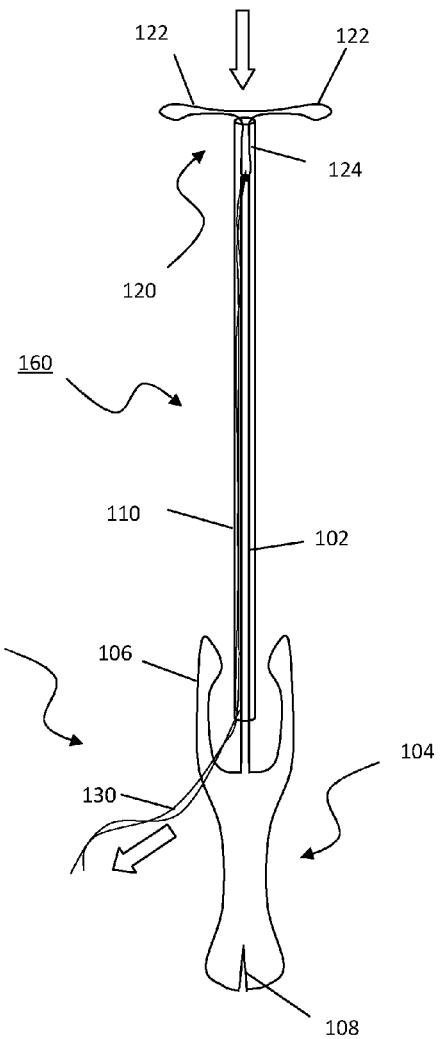

In a second preparatory (priming) step, the inserter (100) is primed as shown in FIG. 13. The protective tube (110) is partially advanced in the distal (30) direction, while the withdrawal string (130) is kept under tension. In order to advance the tube (110), the friction contact surface (152) remains in a state of non-engagement against the protective tube (110); in other words, the tong-shaped gripping mechanism (106) remains relaxed. The central rod (124) of the IUD (120) is covered by the protective tube (110). In a third preparatory step, the inserter (100) is further primed as shown in FIG. 14. The withdrawal string (130) is held under tension and secured firmly using the fastening means (108). The protective tube (110) is advanced (FIG. 15) over the IUD (120). The protective tube (110) may be advance fully over the IUD (120) to cover not only the central rod (124), but also the folded wings (122). Alternatively, the protective tube (110) may be advanced partially over the IUD (120) to cause the wings to fold (122), so that at least the wing tips are exposed. The friction contact surface (152) remains in a state of non-engagement against the protective tube (110); in otherwords, the tong-shaped gripping mechanism (106) remains relaxed.

In a first insertion step, the inserter (100) is advanced into the cervical canal (220), as illustrated in FIG. 16. The withdrawal string (130) is under tension and firmly secured to the fastening mechanism (108). The friction contact surface (152) is frictionally engaged against the protective tube (110); in other words, the gripping mechanism (106) is locked. This is so that the protective tube (110) is immobilized with respect to the plunger (102). This configuration ensures that the IUD (120) remains fully covered during insertion into the cervical canal (220).

During a second insertion step, illustrated in FIG. 17, the distal (30) end of the protective tube (110) has reached a midway point in the cervical canal (220). The withdrawal string (130) remains under tension and firmly secured to the fastening mechanism (108). The friction contact surface (152) is released from frictional engagement against the protective tube (110); in other words, the tong-shaped gripping mechanism (106) is relaxed. This allows for partial retraction in the proximal (20) direction of the protective tube (110) with respect to the plunger (102). This partial retraction uncovers the wings (122) of the IUD (120), which fold out in the uterus (200).

During a third insertion step, the inserter (100) is fully advanced until the fundal position is reached, as shown in FIG. 18. The withdrawal string (130) remains under tension and firmly secured to the fastening mechanism (108). The friction contact surface (152) is frictionally engaged against the protective tube (110); in other words, the gripping mechanism (106) is locked. This is so that the protective tube (110) is immobilized with respect to the plunger (102). This ensures that the IUD (120) remains partially covered by the protective tube (110).

Figure 19:
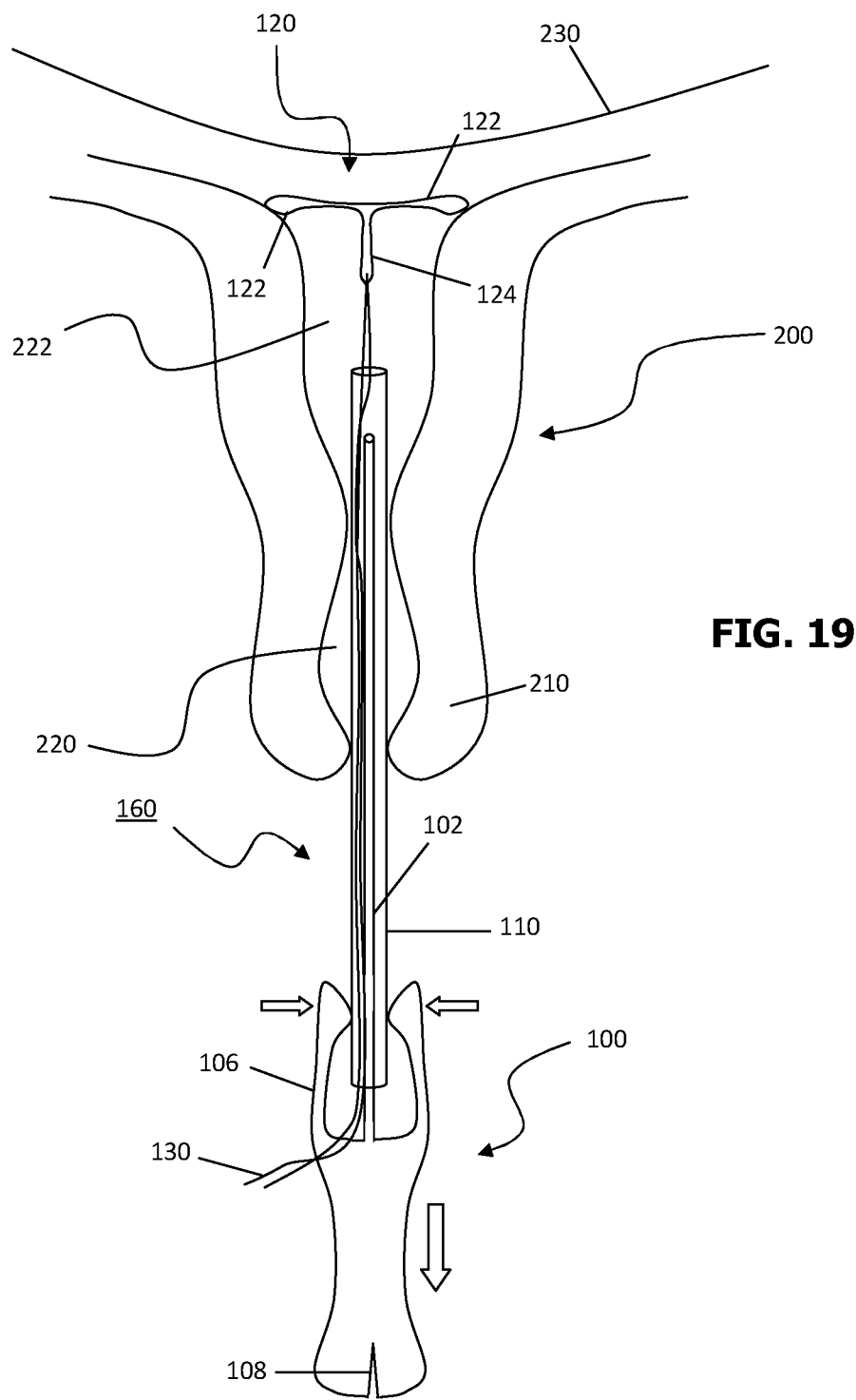
Figure 20:
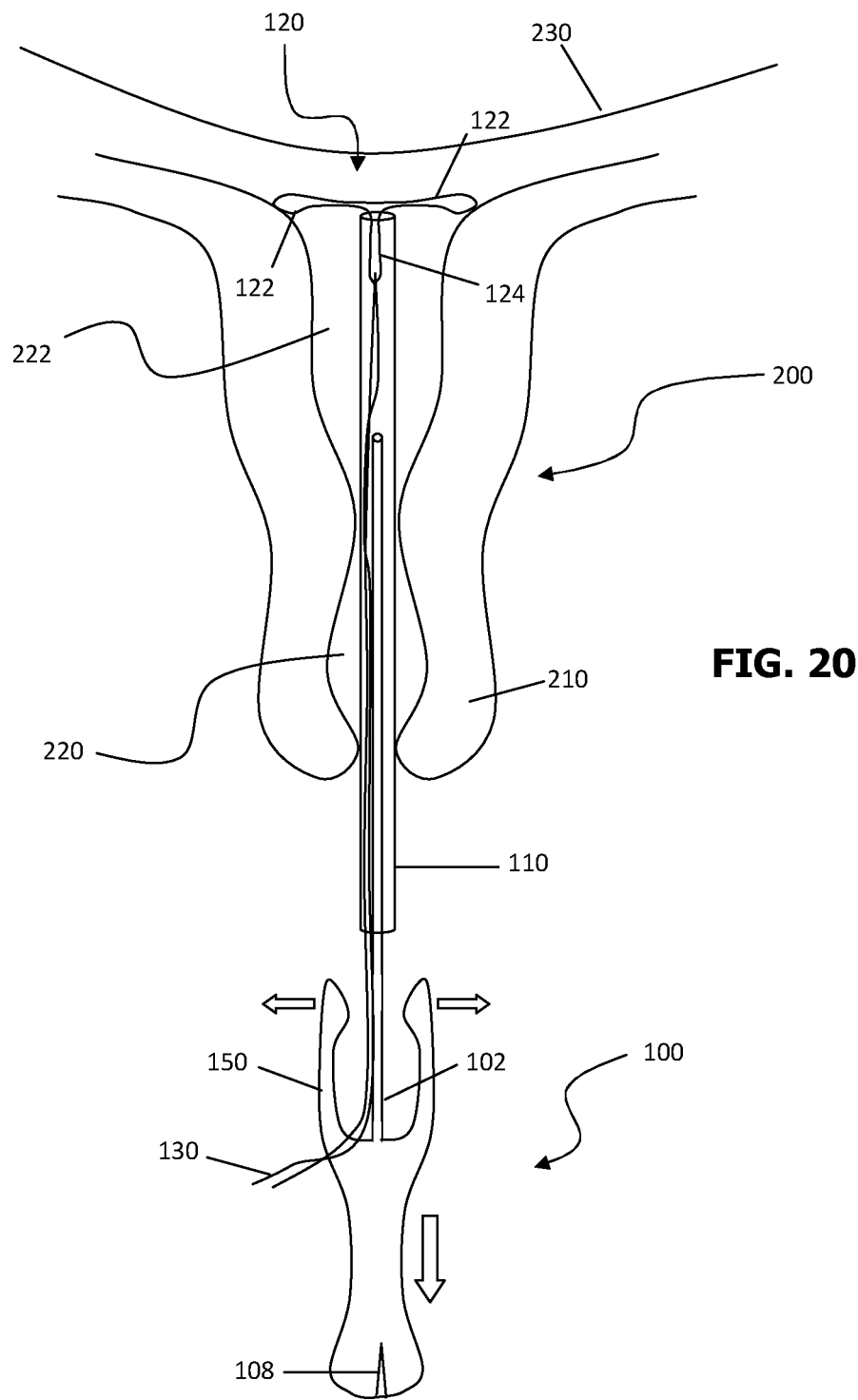

A fourth insertion step, illustrated in FIG. 19, occurs after the inserter (100) is fully advanced. The withdrawal string (130) is released from the fastening means (108) and the withdrawal string (130) is no longer under tension. The friction contact surface (152) remains frictionally engaged against the protective tube (110), so that the protective tube (110) is immobilized with respect to the plunger (102).

In a final step, the inserter (100) is withdrawn from the uterus (200) and the cervical canal (220), as shown in FIG. 19. The withdrawal string (130) remains relaxed, so that the IUD (120) is left behind in the uterus (200). The friction contact surface (152) remains frictionally engaged against the protective tube (110), so that the protective tube (110) is immobilized with respect to the plunger (102). This ensures that the protective tube (110) is also removed from the uterus (200) and cervical canal (220).

Figure 22:
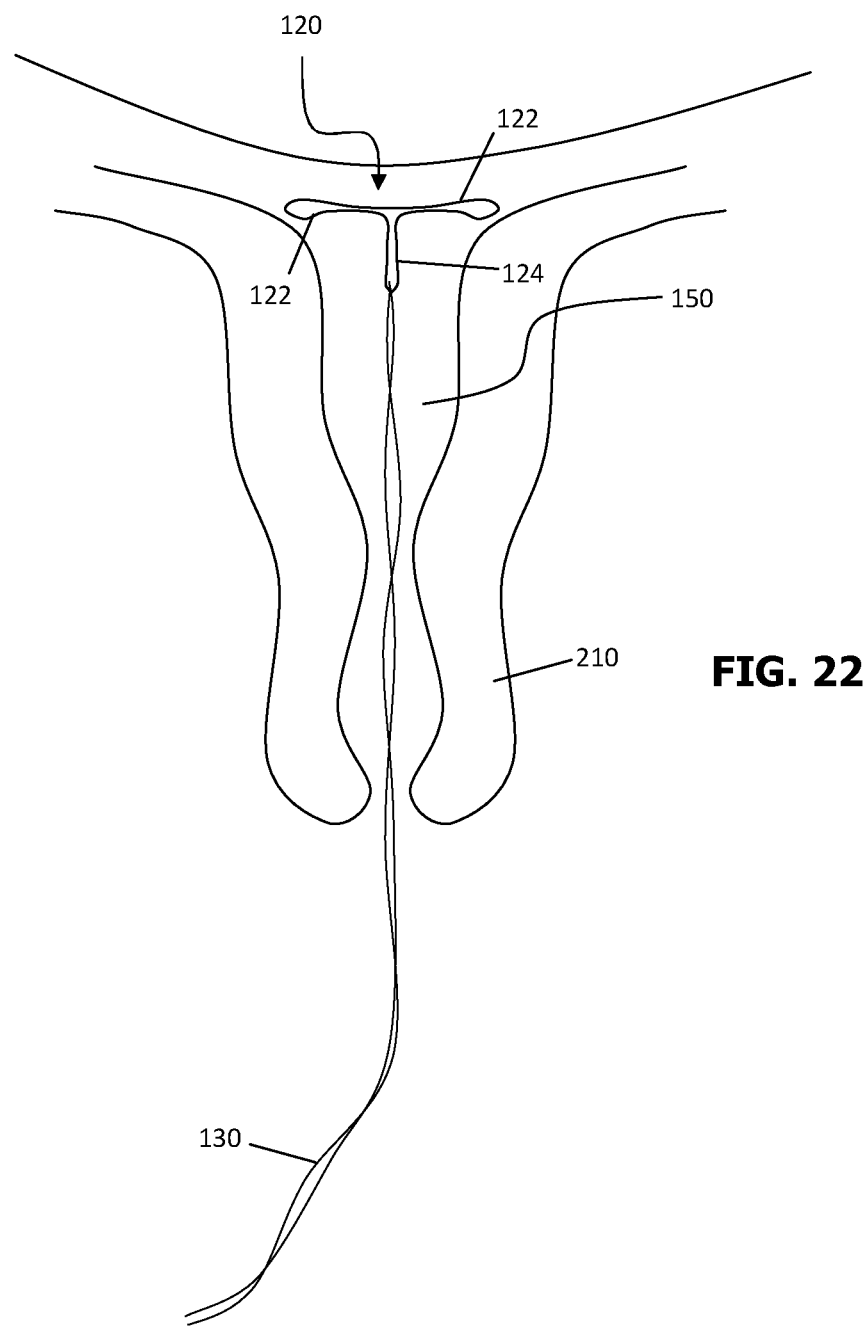

FIG. 22 illustrates the IUD (120) which has been inserted, while the withdrawal string (130) still exits along the cervical canal (220). The inserter (100), including the protective tube (110), has been fully withdrawn.

The invention also relates to the use of an inserter (100) or inserter assembly as described by the aforementioned embodiments for insertion of an IUD.

SOME FURTHER EMBODIMENTS OF THE INVENTION

One embodiment of the invention relates to an inserter (100) for inserting and positioning an intra-uterine device (IUD) (120), which is attached to a withdrawal string (130), said inserter (100) comprising:
  a) a plunger (102), having a proximal and distal end, over which the protective tube (110) can slide, which distal end is configured for dismountable connection with the IUD (120), which protective tube (110) is configured to slidably cover the IUD (120);
  b) a handle (104), which is attached to the proximal end of the plunger (102) and which further comprises a tong-shaped gripping mechanism (106); and
whereby the gripping mechanism (106) is adapted to reversibly lock the position of the protective tube (110) relative to the plunger (102).

Another embodiment of the invention relates to an inserter (100) as described herein, whereby the plunger (102) and handle (104) form one piece.

Another embodiment of the invention relates to an inserter (100) as described above, whereby the plunger (102) and handle (104) are constructed from a polymeric material, selected from a list comprising resin, polycarbonate, polypropylene and a combination thereof.

Another embodiment of the invention relates to an inserter (100) as described above, whereby the inserter (100) is between 15 and 35 cm long, whereby the plunger (102) is between 10 and 30 cm long and whereby the handle (104) is between 1 and 5 cm wide.

Another embodiment of the invention relates to an inserter (100) as described above, whereby the plunger (102) is at least partially preferably entirely solid.

Another embodiment of the invention relates to an inserter (100) as described above, further comprising graduated markings on the plunger (102) configured to define the optimal positions of a protective tube (110) with respect to the plunger (102).

Another embodiment of the invention relates to an inserter (100) as described above, whereby the surface of the plunger (102) and/or gripping mechanism (106) is configured to provide a frictional grip on the protective tube (110).

Another embodiment of the invention relates to an inserter as described above, further comprising serrations on the surface of the plunger (102) and/or the gripping mechanism (106) configured to provide a frictional grip on the protective tube (110).

Another embodiment of the invention relates to an inserter (100) as described above, wherein the handle (106) is further provided with a fastening means (108) configured to secure the withdrawal string (130), optionally under tension.

Another embodiment of the invention relates to an inserter (100) as described above, characterized in that the gripping mechanism (106) is configured to apply a force in a radial direction relative to a central longitudinal axis of the protective tube (110) that reversibly locks the slidable position of the protective tube (110) relative to the plunger (102).

Another embodiment of the invention relates to an inserter (100) as described above, wherein the gripping mechanism (102) applies diametrically opposing radial forces to the protective tube (110).

Another embodiment of the invention relates to an inserter (100) as described above, further comprising the protective tube (110) having a central lumen, through which the plunger (102) is disposed, whereby the distal end of the protective tube (110) is configured for covering the intra-uterine device (IUD) (120).

Another embodiment of the invention relates to an inserter (100) as described above, whereby the protective tube (110) is constructed from a polymeric material.

Another embodiment of the invention relates to an inserter (100) as described above, wherein the protective tube (110) further comprises graduated markings configured to measure the position of the protective tube (110) with respect to the plunger (102).

Another embodiment of the invention relates to an inserter (100) as described above, wherein the protective tube (110) further comprises a collar indicator configured to measure the position of the protective tube (110) with respect to the plunger (102).

Another embodiment of the invention relates to an inserter (100) as described above, further comprising a T-shaped intra-uterine device (IUD) (120) comprising a pair of wings (122) fixed to a central rod (124), positioned at the distal end of the plunger (102).

Another embodiment of the invention relates to an inserter (100) as described above, whereby the T-shaped intra-uterine device (IUD) (120) is coated or impregnated with a medicament.

Another embodiment of the invention relates to an inserter (100) as described above, whereby the T-shaped intra-uterine device (IUD) (120) is partially or wholly constructed from a biocompatible material, a polymeric material, polyethylene, copper, gold, silver or a combination thereof.

Another embodiment of the invention relates to an inserter (100) as described above, whereby the T-shaped intra-uterine device (IUD) (120) is configured as a contraception or as a treatment for menorrhagia.

Another embodiment of the invention relates to an inserter (100) as described above, whereby the wings (122) of the IUD (120) are configured to fold or unfold responsive to the slidable movement of a protective tube (110) that covers or uncovers the wings (122) of the IUD (120).

Another embodiment of the invention relates to an inserter (100) as described above, wherein the IUD further comprises a withdrawal string (130) attached at one end, preferably to the rod (124).

Another embodiment of the invention relates to an inserter (100) as described above, whereby the withdrawal string (130) passes through the protective tube (110) from the distal (30) end to the proximal (20) end.

Another embodiment of the invention relates to an inserter (100) as described above, whereby the withdrawal string (130) is constructed from polyamide.

Another embodiment of the invention relates to an inserter (100) as described above, configured such that tension applied to the withdrawal string (130) maintains the IUD (120) in contact with the distal (30) end of the plunger (100) while the protective tube is advanced at least partially over the IUD.

Another embodiment of the invention relates to an inserter (100) as described above, whereby a proximal (20) end of the withdrawal string (130) is permanently fixed to the handle (104), and under tension to maintain the IUD (120) in contact with the distal end of the plunger (102).

Another embodiment of the invention relates to a method, for inserting and positioning an intra-uterine device (IUD) (120) by use of an inserter (100) as described above, said method comprising the following steps:
  a) covering the IUD (120) with a protective tube (110), while keeping the withdrawal string (130) relaxed;
  b) partially advancing the inserter (100) into the cervical canal, while activating the gripping mechanism (106), while keeping the withdrawal string under tension;
  c) partially withdrawing the protective tube (110), while de-activating the gripping mechanism (106), while keeping the withdrawal string (130) under tension, such that the wings (122) of the IUD (120) are uncovered from the protective tube (110);
  d) fully advancing the inserter (100) into the cervical canal, while activating the gripping mechanism (106), while keeping the withdrawal string (130) under tension; and
  e) fully withdrawing the inserter (100), while activating the gripping mechanism. (106), while releasing the tension on the withdrawal string (130).

Another embodiment of the invention relates to a use of an inserter (100) as described above for insertion of an UID.

What is claimed is:

1. An inserter having a proximal and distal end for inserting and positioning an intra-uterine device (IUD) which is attached to a withdrawal string, comprising:
  a) a plunger, having a central longitudinal axis, configured for slidable mounting of a hollow protective tube, the distal end of the plunger being configured for dismountable connection with the IUD, wherein the protective tube is configured to slidably cover the IUD and move in association with a first slide member different from the protective tube, the first slide member having a first discrete contact element;
  b) a handle attached to the proximal end of the plunger, the handle comprising a second slide member different from the plunger, the second slide member having a second discrete contact element; and
  c) a longitudinal member that forms a part of the handle, which extends in the distal direction with respect to the plunger, wherein the longitudinal member contains a friction contact surface against which the protective tube can frictionally engage, wherein the frictional engagement of the friction contact surface against the protective tube is manually actuatable and wherein the frictional engagement of the friction contact surface against the protective tube increases a resistance to slid the protective tube relative to the plunger, wherein the inserter further comprises the protective tube having a central lumen, through which the plunger is disposed, wherein the distal end of the protective tube is configured for receiving the intra-uterine device (IUD), wherein:

the IUD is a T-shaped IUD comprising a pair of wings, each of the wings has a rounded wing tip, and the wings are fixed to a central rod, said IUD is positioned at the distal end of the plunger;

the protective tube is attached in a fixed relation to the first slide member having the first discrete contact element, and the plunger is attached in a fixed relation to the handle comprising the second slide member having the second discrete contact element, the first and second discrete contact elements are slidable in relation to each other and enclosed within a body of the handle and configured such that they frictionally engage together upon sliding so as to increase the resistance to sliding of the protective tube relative to the plunger selectively at a first discrete position (P1) which corresponds to a position of the protective tube covering at least a part of the wings of the IUD when the central rod of the IUD is engaged with the distal end of the plunger.

2. An inserter having a proximal and distal end for inserting and positioning an intra-uterine device (IUD) which is attached to a withdrawal string, comprising:

a) a plunger having a central longitudinal axis, configured for slidable mounting of a hollow protective tube, the distal end of the plunger being configured for dismountable connection with the IUD, wherein the protective tube is configured to slidably cover the IUD and move in association with a first slide member different from the protective tube, the first slide member having a third discrete contact element;

b) a handle attached to the proximal end of the plunger, the handle comprising a second slide member different from the plunger, the second slide member having a fourth discrete contact element; and c) a longitudinal member that forms a part of the handle, which extends in the distal direction with respect to the plunger, wherein the longitudinal member contains a friction contact surface against which the protective tube can frictionally engage, wherein the frictional engagement of the friction contact surface against the protective tube is manually actuatable and wherein the frictional engagement of the friction contact surface against the protective tube increases resistance to sliding of the protective tube relative to the plunger;

wherein the inserter further comprises the protective tube having a central lumen, through which the plunger is disposed, wherein the distal end of the protective tube is configured for receiving the intra-uterine device (IUD), wherein:

the IUD is a T-shaped IUD comprising a pair of wings, wherein each of the wings has a rounded wing tip, and the wings are fixed to a central rod, said IUD is positioned at the distal end of the plunger; and the protective tube is attached in a fixed relation to the first slide member having the third discrete contact element, and the plunger is attached in a fixed relation to the handle comprising the second slide member having the fourth discrete contact element, the third and fourth discrete contact elements are slidable in relation to each other and enclosed within a body of the handle and configured such that they engage together upon sliding so as to increase the resistance to sliding of the protective tube relative to the plunger selectively at a second discrete position (P2) which corresponds to a location of the protective tube covering at least a part of the IUD central rod, and the wings are unfolded when the central rod of the IUD is engaged with the distal end of the plunger.

3. The inserter according to claim 2 wherein, the protective tube is attached in fixed relation to a first discrete contact element and the plunger is attached in fixed relation to a second discrete contact element, the first and second discrete contact elements being in slidable relation to each other and enclosed within the body of the handle and configured such that they frictionally engage together so increasing the resistance to sliding of the protective tube relative to the plunger selectively at a first discrete position (P1) which corresponds to a position of the protective tube where it covers at least part of the wings of the IUD when the central rod of the IUD is engaged with the distal end of the plunger; and the first and third discrete contact elements are one and the same.

4. An inserter having a proximal and distal end for inserting and positioning an intra-uterine device (IUD) which is attached to a withdrawal string, comprising:

a) a plunger having a central longitudinal axis, configured for slidable mounting of a hollow protective tube, the distal end of the plunger being configured for dismountable connection with the IUD, wherein the protective tube is configured to slidably cover the IUD and move in association with a first slide member different from the protective tube, the first slide member having a fifth discrete contact element;

b) a handle attached to the proximal end of the plunger, the handle comprising a second slide member different from the plunger, the second slide member having a sixth discrete contact element; and c) a longitudinal member that forms a part of the handle, which extends in the distal direction with respect to the plunger, wherein the longitudinal member contains a friction contact surface against which the protective tube can frictionally engage, wherein the frictional engagement of the friction contact surface against the protective tube is manually actuatable and wherein the frictional engagement of the friction contact surface against the protective tube increases resistance to sliding of the protective tube relative to the plunger, wherein the inserter further comprises the protective tube having a central lumen, through which the plunger is disposed, wherein the distal end of the protective tube is configured for receiving the intra-uterine device (IUD), wherein:

the IUD is a T-shaped IUD comprising a pair of wings, wherein each of the wings has a rounded wing tip, and the wings are fixed to a central rod, said IUD is positioned at the distal end of the plunger;

the protective tube is attached in a fixed relation to the first slide member having the fifth discrete contact element, and the plunger is attached in a fixed relation to the handle comprising the second slide member having the sixth discrete contact element, the fifth discrete contact element and sixth discrete contact element are slidable in relation to each other and enclosed within a body of the handle and configured such that they engage upon sliding so as to stop the sliding of the protective tube relative to the plunger selectively at a third discrete position (P3) which corresponds to a location of the protective tube where the IUD central rod is uncovered when the central rod of the IUD is engaged with the distal end of the plunger.

5. The inserter according to claim 4 wherein,
the protective tube is attached in fixed relation to a first discrete contact element and the plunger is attached in fixed relation to a second discrete contact element, the first and second discrete contact elements being in slidable relation to each other and enclosed within the body of the handle and configured such that they frictionally engage together so increasing the resistance to sliding of the protective tube relative to the plunger selectively at a first discrete position (P1) which corresponds to a position of the protective tube where it covers at least part of the wings of the IUD when the central rod of the IUD is engaged with the distal end of the plunger; and the protective tube is attached in fixed relation to a third discrete contact element and the plunger is attached in fixed relation to a fourth discrete contact element, the third and fourth discrete contact elements being in slidable relation to each other and enclosed within the body of the handle and configured such that they engage together so increasing the resistance to sliding of the protective tube relative to the plunger selectively at a second discrete position (P2) which corresponds to a location of the protective tube where it covers at least part of the IUD central rod, and the wings are unfolded when the central rod of the IUD is engaged with the distal end of the plunger, wherein the first, third and fifth discrete contact elements are one and the same.

6. An inserter assembly, comprising:
the inserter according to any of claim 1, 2 or 4, wherein the plunger is disposed with a longitudinal groove for receiving the withdrawal string,
wherein the withdrawal string is attached at one end of the IUD, and the withdrawal string passes along the longitudinal groove for receiving the withdrawal string.

7. The inserter according to any of claim 1, 2 or 4, wherein the longitudinal member is in essentially fixed relation to the plunger, and is configured to receive a force in an essentially radial direction relative to the central longitudinal axis of the plunger, wherein the force is applied by the protective tube upon manual actuation of the protective tube.

8. The inserter according to any of claim 1, 2 or 4, wherein the longitudinal member is in essentially fixed relation to the plunger, and is configured to receive a force in an essentially radial direction relative to the central longitudinal axis of the plunger, wherein the force is applied by the protective tube upon manual actuation of the protective tube and
wherein the friction contact surface is comprised in a longitudinal guiding rail, wherein the protective tube is provided at the proximal end with a cuff, and wherein the longitudinal guiding rail and the cuff are slidably connected.

9. The inserter according to any of claim 1, 2 or 4, wherein the protective tube is provided at the proximal end with a cuff, and the cuff is disposed with a T-shaped protrusion, and the longitudinal member comprises a longitudinal guiding slot along which the T-shaped protrusion slidably engages, allowing the protective tube to slide relative to the longitudinal member.

10. The inserter according to any of claim 1, 2 or 4, wherein the plunger is disposed with a longitudinal groove for receiving the withdrawal string.

11. The inserter according to any of claim 1, 2 or 4, wherein the plunger terminates in a distal tip configured to dismountably couple to the proximal end of the central rod of the IUD.

12. The inserter assembly according to any of claim 1, 2 or 4, wherein the protective tube further comprises a flange, optionally slidable, on the surface of the protective tube configured to abut with the entrance of the cervix to prohibit further insertion of the protective tube into the uterine cavity.

13. A method for priming for insertion into the cervical canal an inserter assembly comprising:
the inserter according to any of claim 1, 2 or 4, wherein wherein the withdrawal string is attached at one end of the IUD, and the withdrawal string passes along a longitudinal groove for receiving the withdrawal string, and
provided with an IUD positioned with the wings outside the protective tube comprising the steps:
a) keeping the withdrawal string relaxed;
b) advancing partially the protective tube distally over the plunger until the protective tube is positioned such that the wing tips of the IUD would partially protrude from the protective tube but are touching when the central rod of the IUD is engaged with the distal end of the plunger;
c) activating frictional engagement of the friction contact surface against the protective tube, so as to fix the position of the protective tube relative to the plunger; and
d) providing tension to the withdrawal string, wherein the IUD enters inside the central lumen of the protective tube until the wings of the IUD are covered by the protective tube and the wing tips of the IUD partially protrude from the protective tube but are touching, and the proximal end of the IUD is engaged with the distal end of the plunger;
e) thereby priming the inserter assembly.

14. A method for priming for insertion into the cervical canal an inserter assembly comprising:
the inserter according to any of claim 1, 2 or 4, wherein the plunger is disposed with a longitudinal groove for receiving the withdrawal string,
wherein the withdrawal string is attached at one end of the IUD, wherein the withdrawal string passes along the longitudinal groove for receiving the withdrawal string, and
provided with an IUD positioned with the wings outside the protective tube comprising the steps:
a) placing the withdrawal string under tension so that the proximal end of the IUD is engaged with the distal end of the plunger; and
b) partially advancing the protective tube distally over the plunger until the wings of the IUD are covered by the protective tube and the wing tips of the IUD partially protrude from the protective tube but are touching;
c) thereby priming the inserter assembly.

* * * * *